(12) United States Patent
Sankaram

(10) Patent No.: US 6,793,938 B2
(45) Date of Patent: Sep. 21, 2004

(54) BIODEGRADABLE COMPOSITIONS FOR THE CONTROLLED RELEASE OF ENCAPSULATED SUBSTANCES

(75) Inventor: Mantripragada Sankaram, San Diego, CA (US)

(73) Assignee: Skye Pharma, Inc., San Diego, CA (US)

( * ) Notice: Subject to any disclaimer, the term of this patent is extended or adjusted under 35 U.S.C. 154(b) by 29 days.

(21) Appl. No.: 09/859,847

(22) Filed: May 17, 2001

(65) Prior Publication Data

US 2001/0048945 A1 Dec. 6, 2001

Related U.S. Application Data

(62) Division of application No. 09/356,218, filed on Jul. 16, 1999, now Pat. No. 6,277,413.
(60) Provisional application No. 60/123,097, filed on Mar. 5, 1999, provisional application No. 60/101,855, filed on Sep. 25, 1998, and provisional application No. 60/093,243, filed on Jul. 17, 1998.

(51) Int. Cl.[7] ................................................. A61K 9/14
(52) U.S. Cl. ...................... 424/489; 424/499; 424/500; 424/501; 424/502; 424/422; 424/423; 424/424; 424/425; 424/426; 424/484
(58) Field of Search ................................ 424/483, 499, 424/500, 501, 502, 484, 422, 423, 424, 425, 426, 450; 264/4.6

(56) References Cited

U.S. PATENT DOCUMENTS

| | | |
|---|---|---|
| 4,588,578 A | 5/1986 | Fountain et al. |
| 4,599,342 A | 7/1986 | LaHann |
| 4,610,868 A | 9/1986 | Fountain et al. |
| 4,622,219 A | 11/1986 | Haynes |
| 4,711,782 A | 12/1987 | Okada et al. |
| 4,725,442 A | 2/1988 | Haynes |
| 4,744,989 A | 5/1988 | Payne et al. |
| 4,761,288 A | 8/1988 | Mezei |
| 4,844,904 A | 7/1989 | Hamaguchi et al. |
| 4,861,597 A | 8/1989 | Kida et al. |
| 4,877,561 A | 10/1989 | Iga et al. |
| 4,877,619 A | 10/1989 | Richer |
| 4,937,078 A | 6/1990 | Mezei et al. |
| 5,000,959 A | 3/1991 | Iga et al. |
| 5,004,611 A | 4/1991 | Leigh |
| 5,013,556 A | 5/1991 | Woodle et al. |
| 5,019,394 A | 5/1991 | Hamaguchi et al. |

(List continued on next page.)

OTHER PUBLICATIONS

Watts et al., "Microencapsulation Using Emulsificaiton/Solvent Evaporation: An Overview of Techniques and Applications," Infotrieve, vol. 7, Issue 3 (1990) 235–259.
Edwards et al., "Large Porous Particles for Pulmonary Drug Delivery," Science, vol. 276, Jun. 20, 1997, www.sciencemag.org, 1868–1871.

*Primary Examiner*—Thurman K. Page
*Assistant Examiner*—Liliana Di Nolan-Baron
(74) *Attorney, Agent, or Firm*—Paul, Hastings, Janofsky & Walker LLP; Diane L. Gardner

(57) ABSTRACT

Pharmaceutical compositions that enable the release of a physiologically active substance over a prolonged period of time following administration to a patient are described. The pharmaceutical compositions are provided by encapsulation of a physiologically active substance into a matrix comprising biodegradable polymers and lipids. The rate of release of the physiologically active substance from the pharmaceutical composition is controlled by varying the ratio of the polymer to the lipid. The compositions can be stored in an aqueous suspension or as a solid dosage form. The physiologically active substances include small molecules, peptides, proteins, nucleic acids and vaccines. The biodegradable polymers include homopolymers, or random or block copolymers. The lipids include phospholipids, cholesterol and glycerides.

9 Claims, 13 Drawing Sheets

U.S. PATENT DOCUMENTS

| | | |
|---|---|---|
| 5,049,392 A | 9/1991 | Weiner et al. |
| 5,141,674 A | 8/1992 | Leigh |
| 5,169,637 A | 12/1992 | Lenk et al. |
| 5,186,941 A | 2/1993 | Callahan et al. |
| 5,192,549 A | 3/1993 | Barenolz et al. |
| 5,225,212 A | 7/1993 | Martin et al. |
| 5,227,165 A | 7/1993 | Domb et al. |
| 5,244,678 A | 9/1993 | Legros et al. |
| 5,364,632 A | 11/1994 | Benita et al. |
| 5,393,530 A | 2/1995 | Schneider et al. |
| 5,422,120 A | 6/1995 | Kim .................. 424/450 |
| 5,451,408 A | 9/1995 | Mezei et al. |
| 5,455,044 A | 10/1995 | Kim et al. .......... 424/450 |
| 5,543,158 A | 8/1996 | Gref et al. .......... 424/501 |
| 5,635,205 A | 6/1997 | Nyqvist et al. |
| 5,662,931 A | 9/1997 | Munechika et al. |
| 5,708,011 A | 1/1998 | Bardsley et al. |
| 5,723,147 A | 3/1998 | Kim et al. .......... 424/450 |
| 5,766,627 A | 6/1998 | Sankaram et al. ....... 424/450 |
| 5,770,222 A | 6/1998 | Unger et al. |
| 5,808,573 A | 9/1998 | Shih et al. |
| 5,814,335 A | 9/1998 | Webb et al. |
| 5,827,533 A | 10/1998 | Needham |
| 5,849,763 A | 12/1998 | Bardsley et al. |
| 5,853,755 A | 12/1998 | Foldvari |
| 5,865,184 A | 2/1999 | Takiguchi |
| 5,882,679 A | 3/1999 | Needham |
| 5,891,842 A | 4/1999 | Kream |
| 5,895,661 A | 4/1999 | Tournier et al. |
| 5,910,502 A | 6/1999 | Gennery |
| 5,912,271 A | 6/1999 | Brodin et al. |
| 5,919,804 A | 7/1999 | Gennery |
| 5,922,340 A | 7/1999 | Berde et al. |
| 5,945,435 A | 8/1999 | Evetts |
| 5,955,479 A | 9/1999 | Bardsley et al. |
| 5,962,532 A | 10/1999 | Campbell et al. |
| 5,977,326 A | 11/1999 | Scheinmann et al. |
| 5,980,927 A | 11/1999 | Nelson et al. |
| 5,993,850 A * | 11/1999 | Sankaram et al. .......... 424/450 |
| 6,020,004 A * | 2/2000 | Shah .................. 424/501 |
| 6,046,187 A | 4/2000 | Berde et al. |
| 6,048,545 A | 4/2000 | Keller et al. |
| 6,066,331 A | 5/2000 | Barenholz et al. |
| 6,069,155 A | 5/2000 | Mather et al. |
| 6,103,741 A | 8/2000 | Bardsley et al. |
| 6,120,797 A | 9/2000 | Meers et al. |
| 6,149,937 A | 11/2000 | Camu et al. |
| 6,221,401 B1 | 4/2001 | Zasadzinski et al. |
| 6,238,702 B1 | 5/2001 | Berde et al. |
| 6,248,345 B1 | 6/2001 | Goldenheim et al. |
| 6,287,587 B2 | 9/2001 | Shigeyuki et al. |
| 6,399,094 B1 | 6/2002 | Brandl et al. |
| 6,417,201 B1 | 7/2002 | Bardsley et al. |
| 2001/0004644 A1 | 6/2001 | Levin |
| 2001/0055607 A1 | 12/2001 | Levin |
| 2002/0041895 A1 | 4/2002 | Gregoriadis |

* cited by examiner

BIODEGRADABLE COMPOSITIONS FOR THE CONTROLLED RELEASE OF ENCAPSULATED SUBSTANCES

This application is a divisional of U.S. patent application Ser. No. 09/356,218, filed Jul. 16, 1999 now issued U.S. Pat. No. 6,277,413, and claims the benefit of U.S. Provisional Applications Serial No. 60/093,243, filed July 17, 1998; Serial No. 60/101,855, filed Sep. 25, 1998; Serial No. 60/123,097, filed Mar. 5, 1999.

BACKGROUND OF THE INVENTION

The invention relates to lipid/polymer-containing biodegradable pharmaceutical compositions which are designed to provide controlled release of encapsulated physiologically active substances.

Delivery systems offer the advantage of improved bioavailability and a higher therapeutic index over a prolonged period of time for physiologically active substances. Two major classes of drug-delivery systems are formed from either biodegradable polymers or lipids (Langer, R., *Nature* 392: 5–10, 1998). Polymer-based drug-delivery systems have been developed as microspheres for injection, implants, transdermal patches, and aerosols for inhalation (Domb et al., *Handbook of Biodegradable Polymers*, Harwood Academic Publishers, Amsterdam, 1997; Putney et al., *Nature Biotechnology* 16: 153–157, 1998; Edwards et al., *Science* 276: 1868–1871, 1997). Lipid-based drug delivery systems have been developed as unilamellar, multilamellar (Gregoriadis, *Liposome Technology*, Vols. I, II, III, CRC Press, Boca Raton, Fla., 1993) and multivesicular liposomes (U.S. Pat. No. 5,422,120 to Kim; U.S. Pat. No. 5,723,147 to Kim et al.; U.S. Pat. No. 5,767,627 to Sankaram et al.; U.S. patent application Ser. No. 08/305,158; U.S. patent application Ser. Nos. 08/723,583, 08/925,532, 08/792,566, and 08/925,531).

One of the limitations of using biodegradable polymers is that pharmaceutical compositions such as microspheres prepared from biodegradable polymers require storage under anhydrous conditions due to their susceptibility to hydrolysis. As a result, a typical pharmaceutical package of microspheres for injection consists of one vial with an anhydrous formulation of a biodegradable polymer and a physiologically active substance as a solid dosage form and another vial with an aqueous reconstitution medium (e.g., Lupron Depot, *Physicians Desk Reference*, pp. 2739–2746, Medical Economics Company, Inc., Montvale, N.J., 1997). The contents of the two vials are mixed immediately prior to injection.

Microspheres are prepared by a single emulsification process (U.S. Pat. No. 4,389,330 to Tice et al.; U.S. Pat. No. 3,691,090 to Kitajima et al.), a double emulsification process (Edwards et al., *Science* 276: 1868–1871, 1997), a phase inversion microencapsulation process (Mathiowitz et al., *Nature* 386: 410–413, 1997), or an atomization-freeze process (Putney and Burke, *Nature Biotechnology* 16: 153–157, 1998). In the single emulsification process, a volatile organic solvent phase containing a biodegradable polymer, an aqueous solution necessarily containing an emulsifier such as polyvinyl alcohol, and a physiologically active substance are homogenized to produce an emulsion. The solvent is evaporated and the resulting hardened microspheres are freeze-dried.

In the double emulsification process, an aqueous solution which may contain a physiologically active substance and an volatile organic solvent phase containing a biodegradable polymer are homogenized to form an emulsion. The emulsion is mixed with another aqueous solution, which contains an emulsifier such as polyvinyl alcohol. Evaporation of the solvent and freeze-drying produces microspheres.

In the phase inversion microencapsulation process, drug is added to a dilute polymer solution in a solvent (e.g. dichloromethane) which is then poured rapidly into an unstirred bath of another liquid (e.g. petroleum ether) causing nano- and microspheres to form spontaneously. In the atomization-freeze process, micronized solid physiologically active substance is suspended in a solvent phase containing a biodegradable polymer that is then atomized using sonication or air-atomization. This produces droplets that are then frozen in liquid nitrogen. Addition of another solvent in which both the polymer and the drug are insoluble extracts the solvent from the microspheres.

Microspheres prepared by the single-emulsification process or the double-emulsification process methods can be aerosolized (Edwards et al., *Science* 276: 1868–1871, 1997). Addition of dipalmitoyl phosphatidylcholine to the solvent phase increases particle size, porosity, and efficiency of aerosolization and decreases the mass density. However, formation of the large porous particles still requires an emulsifier such as polyvinyl alcohol. Sucrose stearate, magnesium stearate, aluminum tristearate, sorbitan fatty esters, and polyoxyethylene fatty ethers have been used as droplet stabilizers in a solvent evaporation method for producing microspheres from acrylic polymers (Yuksel et al., *J. Microencapsulation* 14: 725–733, 1997). Poloxamer 188, or Pluronic F68, has been used as a nonionic surfactant in the primary emulsion, in addition to polyvinyl alcohol in the second aqueous phase, for producing microspheres from poly(lactide) using a double emulsification process (Nihant et al., *Pharm. Res.* 11: 1479–1484, 1994). The hydrophilic additives, 2-hydroxypropyl β-cyclodextrin, methyl β-cyclodextrin, Pluronic F-127, L-tartaric acid dimethyl ester, and a hydrophobic additive, beeswax (which consists of esters of long-chain monohydric alcohols with even-numbered carbon chains, esterified with long-chain acids, also having even numbers of carbon atoms) were used to produce poly(lactide-glycolide) double-layer films (Song et al., *J. Controlled Rel.* 45: 177–192, 1997).

SUMMARY OF THE INVENTION

The invention is based on the discovery that biodegradable microspheres can be produced which include both polymer and lipid components, and are free of surfactants introduced into a second aqueous phase of the microspheres. A typical surfactant which heretofore had been introduced into the second aqueous phase is polyvinyl alcohol. Production of the biodegradable microspheres of the invention involves substantial or complete removal of volatile organic solvent from the microsphere walls. The microspheres can be loaded with physiologically active substances, which are released in vitro and in vivo. The rate of release can be easily controlled by adjustments of the lipid/polymer ratio. Previously available microsphere compositions required a change in the identity of the polymer.

In one aspect, the invention provides a lipid/polymer-containing pharmaceutical composition including a biodegradable microsphere which includes at least one type of biodegradable polymer which is soluble in organic solvents, and at least one type of lipid. Also included in the composition is a physiologically active substance which is releasable from the biodegradable microsphere. The composition is preferably substantially free of volatile organic solvent, and most preferably substantially free of polyvinyl alcohol. The compositions can be in the form of an aqueous suspension, or alternatively in the form of a solid dosage, such as in the tablet, capsule, wafer, transdermal patch, suture, implant, or suppository form.

The biodegradable polymers can be homopolymers such as polylactides, polyglycolides, poly(p-dioxanones), polycaprolactones, polyhydroxyalkanoates, polypropylenefumarates, polyorthoesters, polyphosphate esters, polyanhydrides, polyphosphazenes, polyalkylcyanoacrylates, polypeptides, or genetically engineered polymers. At the same time, the biodegradable polymers can be copolymers (random or block) such as poly(lactide-glycolides), poly(p-dioxanone-lactides), poly(p-dioxanone-glycolides), poly(p-dioxanone lactide-glycolides), poly(p-dioxanone-caprolactones), poly(p-dioxanone-alkylene carbonates), poly(p-dioxanone-alkylene oxides), poly(p-dioxanone-carbonate-glycolides), poly(p-dioxanone-carbonates), poly(caprolactone-lactides), poly(caprolactone-glycolides), poly(hydroxyalkanoates), poly(propylenefumarates), poly(orthoesters), poly(ether-esters), poly(ester-amides), poly(ester-urethanes), polyphosphate esters, polyanhydrides, poly(ester-anhydrides), polyphosphazenes, polypeptides and genetically engineered copolymers. The lipids of the pharmaceutical compositions can be zwitterionic lipids, acidic lipids, cationic lipids, sterols, or triglycerides of many types, including many phospholipids.

The physiologically active substances can be hydrophilic, in which case the compositions desirably also include a triglyceride, or they can be hydrophobic, in which case the composition can be substantially free of triglycerides, or they can be amphipathic. The physiologically active substances can be generally classified as antianginas, antiarrhythmics, antiasthmatic agents, antibiotics, antidiabetics, antifingals, antihistamines, antihypertensives, antiparasitics, antineoplastics, antivirals, cardiac glycosides, cytokines such as erythropoietin, herbicides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides, and combinations thereof.

In another aspect, the invention provides a way to vary the rate of release of physiologically active substances by varying the lipid to polymer ratio in the compositions of the invention.

In yet another aspect, the invention provides a method for producing biodegradable lipid/polymer compositions of the invention, including a) forming a water-in-oil type emulsion, which includes a first aqueous phase and a volatile organic phase, b) dispersing the emulsion in a second aqueous phase to form solvent spherules, and c) removing the volatile organic solvent to form the lipid/polymer-containing compositions. A pharmaceutically active substance can be included in the process of making the water-in-oil type emulsion, to produce a pharmaceutical composition. The organic solvent is preferably substantially completely removed.

In a further aspect of the invention, pharmaceutical compositions produced by the above process are provided. If the process involves the use of a hydrophilic pharmaceutically active substance, the process further includes a triglyceride in the process of making the water-in-oil type emulsion.

In a further aspect, the invention provides a method of treating a patient with the pharmaceutical compositions of the invention.

One objective of the present invention is to provide a novel pharmaceutical composition as a drug-delivery system with a physiologically active substance encapsulated within, the composition enabling release of the substance over a prolonged period of time. Another objective is to provide a means of controlling the rate of release of the substance from the composition. Another objective is to provide a means of storing the composition either as a solid dosage form or a semi-solid dosage form.

Preparation of microspheres from biodegradable polymers according to the prior art requires that polyvinyl alcohol be used in the second aqueous solution of a double emulsification process. When an emulsifier such as polyvinyl alcohol is not included in the second aqueous phase of a double emulsion process, the physiologically active substance cannot be encapsulated in prior art microspheres. The compositions of the present invention do not use polyvinyl alcohol in the second aqueous solution. Polyvinyl alcohol is also not utilized in any other aqueous solution for the pharmaceutical compositions of the present invention. In addition to polyvinyl alcohol, the present compositions do not include sucrose stearate, magnesium stearate, aluminum tristearate, sorbitan fatty esters, polyoxyethylene fatty ethers, Poloxamer 188, Pluronic F68, 2-hydroxypropyl β-cyclodextrin, methyl β-cyclodextrin, Pluronic F-127, or L-tartaric acid dimethyl ester.

Rather, the volatile organic solvent phase contains a mixture of lipids and biodegradable polymer. Higher yield and a greater loading of the physiologically active substance are obtained for the lipid/polymer-containing pharmaceutical compositions of the present invention than for polymer microspheres of the prior art.

A variety of physiologically active substances can be encapsulated into the pharmaceutical compositions of the present invention. The useful substances include small molecules, peptides, proteins and nucleic acids. A variety of biodegradable polymers with different lactide:glycolide ratios and different molecular weights can be used for preparing the pharmaceutical compositions of the present invention.

The lipid composition can be varied in order to optimize yield and loading of the physiologically active substance. Thus, there is no requirement of changing the identity of the polymer to affect the loading, yield or release rate of the physiologically active substances to be released. For hydrophobic physiologically active substances, excellent yields and loading are obtained when the pharmaceutical composition does not contain a triglyceride. For hydrophilic physiologically active substances, yield and loading are excellent when the pharmaceutical composition contains a triglyceride.

The pharmaceutical compositions of the present invention afford release of the physiologically active substance into physiological fluids in vitro over a sustained period. Encapsulated physiologically active substances are released into human plasma with sustained release characteristics under two different assay conditions. Varying the lipid:polymer ratio in the pharmaceutical composition can control the rate of release of the physiologically active substance. Controlling the release rate allows one to ensure that the concentration of physiologically active substance is constantly within the therapeutic window; that is, within a concentration range that is high enough to be efficacious, but not so high as to be toxic.

The pharmaceutical compositions of the present invention also afford release of the physiologically active substance in viva over a sustained period. Serum concentrations of physiologically active substances determined at various times after administration in the unencapsulated form, encapsulation in a lipid-only composition, encapsulation in a polymer-only composition, and encapsulation in a lipid/polymer-containing composition of the present invention show that the serum concentration of physiologically active substances peaked at a later time, and was higher for the inventive pharmaceutical compositions than that observed for the other three compositions. Alternately, those encapsulated physiologically active substances which inhibit the release of endogenous serum components (for example, hormones, enzymes, proteins, carbohydrates and the like) show a decrease in the serum concentration of the inhibited component which was longer lasting than that observed for unencapsulated physiologically active substance.

Microsphere compositions prepared from biodegradable polymers according to the prior art are not suitable for storage in aqueous media since the polymer degrades rapidly upon exposure to hydrous conditions. However, the polymer in the lipid/polymer-containing compositions of the present invention is protected against hydrolysis both in accelerated stability studies with heat and acid stress and under normal storage conditions.

The term "solvent spherule" as used throughout the specification and claims means a microscopic spheroid droplet of organic solvent, within which are multiple smaller droplets of a first aqueous solution. The solvent spherules are suspended and totally immersed in a second aqueous solution. The term "releasable from biodegradable microspheres" refers to the condition that upon sufficient biodegradation of the microspheres, the physiologically active substance (encapsulated within the microsphere) is able to exert its physiological effect. Implicit in the definition is the idea that when the substance is not released, its effect is diminished to the extent that a physiological effect is not observable. The physiologically active substances can be released from not only the interior of a microsphere, but also from the microsphere wall (matrix). If the physiologically active substance is attached or appended to the matrix, physical separation of the microsphere and matrix is not required for "release from the biodegradable microsphere". The term "therapeutically effective" as it pertains to the compositions of this invention, means that a physiologically active substance present in the microspheres is released in a manner sufficient to achieve a particular level of treatment of a disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
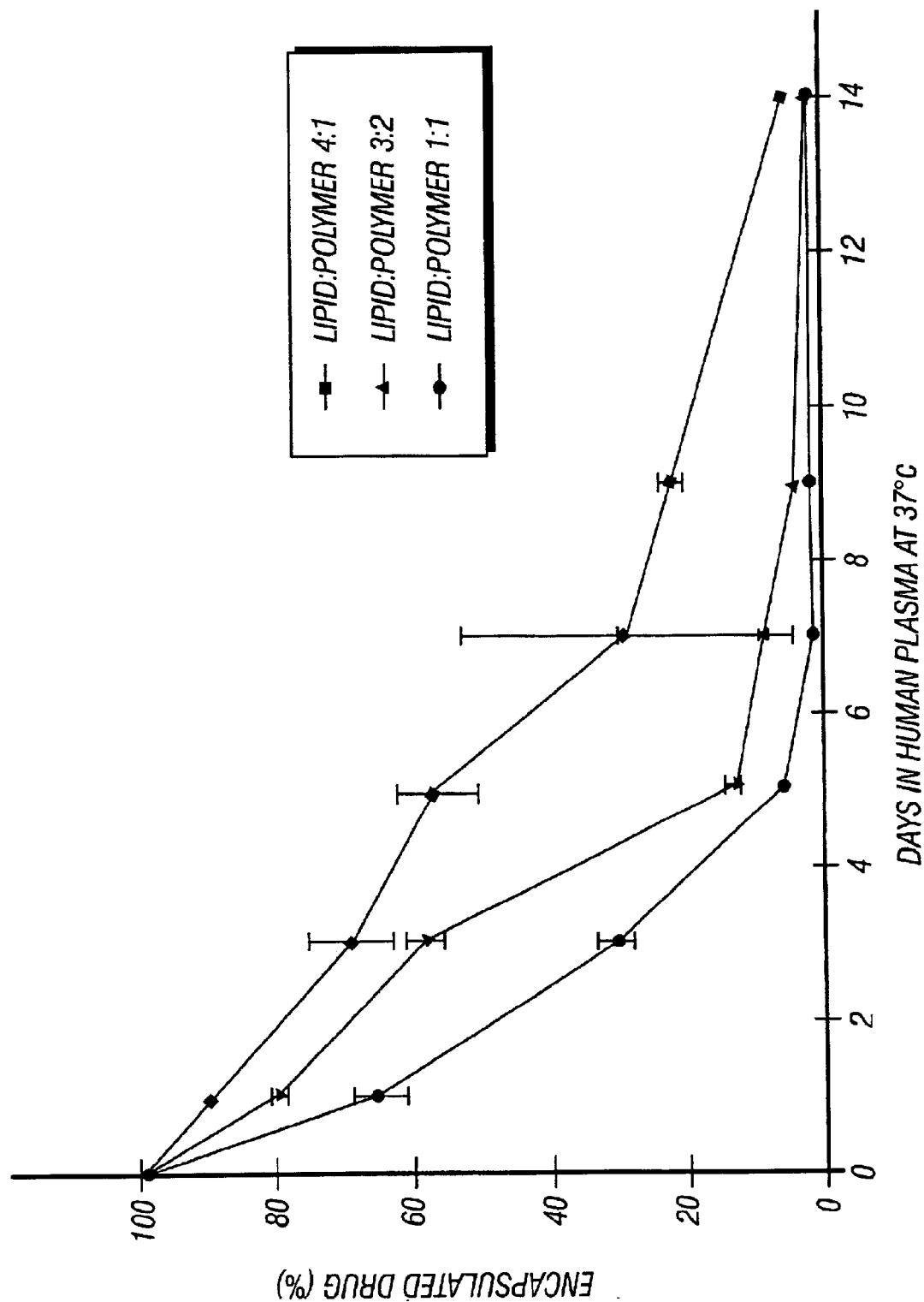
FIG. 1 is a plot of the percentage of encapsulated cytarabine from various lipid/polymer-containing pharmaceutical compositions prepared from cytarabine in hydrochloric acid under static conditions versus time in vitro.

The invention features lipid/polymer-containing compositions that can be loaded with physiologically active substances to provide sustained release in vitro and in vivo. The resulting pharmaceutical compositions can be formulated to yield a range of release rates. The pharmaceutical compositions possess excellent yield and loading characteristics for a variety of physiologically active substances.

Biodegradable Polymer

The lipid/polymer-containing compositions of the invention contain at least one type of biodegradable polymer. The biodegradable polymer may be a homopolymer, or a random or block copolymer, or a blend or physical mixture thereof, with the limitation that the polymer be soluble in volatile organic solvents. Unless the optical activity of a particular material is designated by [L]- or [D]-, the material is presumed to be achiral or a racemic mixture. Meso compounds (those compounds with internally canceling optical activity) are also envisioned as being useful in the present invention.

A biodegradable polymer is one that can be degraded to a low molecular weight and may or may not be eliminated from a living organism. The products of biodegradation may be the individual monomer units, groups of monomer units, molecular entities smaller than individual monomer units, or combinations of such products. Such polymers can also be metabolized by organisms. Biodegradable polymers can be made up of biodegradable monomer units. A biodegradable compound is one that can be acted upon biochemically by living cells or organisms, or parts of these systems, or reagents commonly found in such cells, organisms, or systems, including water, and broken down into lower molecular weight products. An organism can play an active or passive role in such processes.

The biodegradable polymer chains useful in the invention preferably have molecular weights in the range 500 to 5,000,000. The biodegradable polymers can be homopolymers, or random or block copolymers. The copolymer can be a random copolymer containing a random number of subunits of a first copolymer interspersed by a random number of subunits of a second copolymer. The copolymer can also be block copolymer containing one or more blocks of a first copolymer interspersed by blocks of a second copolymer. The block copolymer can also include a block of a first copolymer connected to a block of a second copolymer, without significant interdispersion of the first and second copolymers.

Biodegradable homopolymers useful in the invention can be made up of monomer units selected from the following groups: hydroxy carboxylic acids such as α-hydroxy carboxylic acids including lactic acid, glycolic acid, lactide (intermolecularly esterified dilactic acid), and glycolide (intermolecularly esterified diglycolic acid); β-hydroxy carboxylic acids including β-methyl-β-propiolactone; γ-hydroxy carboxylic acids δ-hydroxy carboxylic acids; and ε-hydroxy carboxylic acids including ε-hydroxy caproic acid; lactones such as: β-lactones; γ-lactones; δ-lactones including valerolactone; and ε-lactones such as ε-caprolactone; benzyl ester-protected lactones such as benzyl malolactone; lactams such as: β-lactams; γ-lactams; δ-lactams; and ε-lactams; thiolactones such as 1,4-dithiane-2,5-dione; dioxanones; unfunctionalized cyclic carbonates such as: trimethylene carbonate, alkyl substituted trimethylene carbonates, and spiro-bis-dimethylene carbonate (2,4,7,9-tetraoxa-spiro[5.5]undecan-3,8-dione); anhydrides; substituted N-carboxy anhydrides; propylene fumarates; orthoesters; phosphate esters; phosphazenes; alkylcyanoacrylates; aminoacids; polyhydroxybutyrates; and substituted variations of the above monomers.

The use of such monomers results in homopolymers such as polylactide, polyglycolide, poly(p-dioxanone), polycaprolactone, polyhydroxyalkanoate, polypropylenefumarate, polyorthoesters, polyphosphate esters, polyanhydrides, polyphosphazenes, polyalkylcyanoacrylates, polypeptides, or genetically engineered polymers, and other homopolymers which can be formed from the above mentioned examples of monomers. Combinations of these homopolymers can also be used to prepare the microspheres of the pharmaceutical compositions of the invention.

The biodegradable copolymers can be selected from poly (lactide-glycolide), poly(p-dioxanone-lactide), poly(p-dioxanone-glycolide), poly(p-dioxanone-lactide-glycolide), poly(p-dioxanone-caprolactone), poly(p-dioxanone-alkylene carbonate), poly(p-dioxanone-alkylene oxide), poly(p-dioxanone-carbonate-glycolide), poly(p-dioxanone-carbonate), poly(caprolactone-lactide), poly(caprolactone-glycolide), poly(hydroxyalkanoate), poly (propylenefumarate), poly(ortho esters), poly(ether-ester), poly(ester-amide), poly(ester-urethane), polyphosphate esters, polyanhydrides, poly(ester-anhydride), polyphospazenes, polypeptides or genetically engineered polymers. Combinations of these copolymers can also be used to prepare the microspheres of the pharmaceutical compositions of the invention.

Preferred biodegradable polymers are polylactide, and poly(lactide-glycolide). In some lactide-containing embodiments, the polymer is prepared by polymerization of a composition including lactide in which greater than about 50% by weight of the lactide is optically active and less than 50% is optically inactive, i.e., racemic [D,L]-lactide and meso [D,L]-lactide. In other embodiments, the optical activity of the lactide monomers is defined as [L], and the lactide monomers are at least about 90% optically active [L]-lactide. In still other embodiments, the lactide monomers are at least about 95% optically active [L]-lactide.

Lipids

The lipid/polymer-containing compositions include at least one type of lipid. The lipids may be natural or synthetic in origin and include phospholipids, sphingolipids, sphingophospholipids, sterols and glycerides. The lipids to be used in the compositions of the invention are generally amphipathic, meaning that they have a hydrophilic "head" group and a hydrophobic "tail" group, and may have membrane-forming capability. The phospholipids and sphingolipids may be anionic, cationic, nonionic, acidic or zwitterionic (having no net charge at their isoelectric point), wherein the two hydrocarbon chains of the lipids are typically between 12 and 22 carbons atoms in length, and have varying degrees of unsaturation. Preferred anionic phospholipids include phosphatidic acids, phosphatidylserines, phosphatidylglycerols, phosphatidylinositols and cardiolipins. Preferred zwitterionic phospholipids are phosphatidylcholines, phosphatidylethanolamines and sphingomyelins. Preferred cationic lipids are diacyl dimethylammonium propanes, acyl trimethylammonium propanes, and stearylamine. Preferred sterols are cholesterol, ergosterol, nanosterol, or esters thereof. The glycerides can be monoglycerides, diglycerides or triglycerides including triolein, and can have varying degrees of unsaturation, with the limitation that the fatty acid hydrocarbon chains of the glycerides are typically between 12 and 22 carbons atoms in length, and have varying degrees of unsaturation. Combinations of these lipids can also be used to prepare the microspheres of the pharmaceutical compositions of the invention.

Physiologically Active Substance

Physiologically active substance means a natural, synthetic or genetically engineered chemical or biological compound that is known in the art as having utility for modulating physiological processes in order to afford diagnosis of, prophylaxis against, or treatment of, an undesired existing condition in a living being. Physiologically active substances include drugs such as antianginas, antiarrhythmics, antiasthmatic agents, antibiotics, antidiabetics, antifungals, antihistamines, antihypertensives, antiparasitics, antineoplastics, antitumor drugs, antivirals, cardiac glycosides, herbicides, hormones, immunomodulators, monoclonal antibodies, neurotransmitters, nucleic acids, proteins, radio contrast agents, radionuclides, sedatives, analgesics, steroids, tranquilizers, vaccines, vasopressors, anesthetics, peptides and the like.

Of particular interest are semisynthetic amino glycoside antibiotics including amikacin; antidiabetics; peptides such as insulin; antitumor drugs including paclitaxel; antineoplastics including cytarabine, 5-fluorouracil, leuprolide, and floxuridine; alkaloid opiate analgesics including morphine and hydromorphone; local anesthetics including bupivacaine, synthetic anti-inflammatory adrenocortical steroids including dexamethasone; antimetabolites including methotrexate; glycopeptide antibiotics including bleomycin; vincaleukoblastines and stathmokinetic oncolytic agents including vincristine and vinblastine; hormones such as erythropoietin, plasma proteins, cytokines, growth factors, DNA and RNA from a variety of organisms, and antisense oligonucleotides. Prodrugs which undergo conversion to the indicated physiologically active substances upon local interactions with the intracellular medium, cells, or tissues can also be employed in the invention. Any pharmaceutically acceptable salt of a particular physiologically active substance which is capable of forming such a salt is also envisioned as useful in the present invention, including halide salts, phosphate salts, acetate salts, and other salts.

The physiologically active substances may be used alone or in combination with the limitation that the amount of the substance in the pharmaceutical composition be sufficient to enable the diagnosis of, prophylaxis against, or the treatment of, an undesired existing condition in a living being. Generally, the dosage will vary with the age, condition, sex, and extent of the undesired condition in the patient, and can be determined by one skilled in the art. The dosage range appropriate for human use includes a range of 0.1 to 6,000 mg of the physiologically active substance per square meter of body surface area.

The pharmaceutical compositions of the invention can be administered parenterally by injection or by gradual infusion over time. The compositions can be administered intravenously, intraperitoneally, intramuscularly, subcutaneously, intracavity, or transdermally. Other methods of administration will be known to those skilled in the art. For some applications, such as subcutaneous administration, the dose required may be quite small, but for other applications, such as intraperitoneal administration, the required dose may be very large. While doses outside the foregoing dosage range may be given, this range encompasses the breadth of use for practically all physiologically active substances. The pharmaceutical compositions of the invention can also be administered enterally.

Double Emulsification Process

The double emulsification process comprises a three-step process producing a semi-solid dosage form of the pharmaceutical composition of the invention. First, a "water-in-oil"-type emulsion is formed from a first aqueous phase and a volatile organic solvent phase, wherein the emulsion contains a physiologically active substance in either the first aqueous or volatile organic solvent phase and the volatile organic solvent phase includes at least one type of biodegradable polymer or copolymer and at least one type of lipid. If the physiologically active substance is hydrophilic, it is present in the first aqueous phase, and if the physiologically active substance is hydrophobic, it is present in the volatile organic solvent phase. Physiologically active substances that are amphipathic can be present in either the first aqueous phase or the volatile organic solvent phase or in both phases.

The "water-in-oil"-type emulsion is characterized by the presence of disconnected isolated aqueous droplets dispersed in a continuous matrix formed by the volatile organic solvent phase. Ethers, hydrocarbons, halogenated hydrocarbons may be used as the volatile organic solvent. Preferred volatile organic solvents are chloroform, dichloromethane, diethyl ether, isopropyl ether, and combinations thereof. The first aqueous phase may contain excipients such as osmotic spacers, acids, bases, buffers, nutrients, supplements or similar compounds. The "water-in-oil"-type emulsion can be produced by mechanical agitation such as by ultrasonic energy, nozzle atomization, by the use of static mixers, impeller mixers or vibratory-type mixers. Forcing the phases through a porous pipe to produce uniform sized emulsion particles can also form such emulsions. These methods result in the formation of solvent spherules.

Second, the solvent spherules which are formed from the first "water-in-oil"-type emulsion are introduced into a second aqueous phase and mixed, analogously as described for the first step. The second aqueous phase can be water, or may contain electrolytes, buffer salts, or other excipients well known in the art of semi-solid dosage forms, and preferably contains glucose and lysine.

In the third step, the volatile organic solvent is removed, generally by evaporation, for instance, under reduced pressure or by passing a stream of gas over or through the spherules. Representative gases satisfactory for use in evaporating the solvent include nitrogen, helium, argon, carbon dioxide, air or combinations thereof. When the solvent is substantially or completely removed, the lipid/polymer-containing composition is formed with the first aqueous solution encapsulated in biodegradable microspheres formed from the polymer and lipid components, with the microspheres suspended in the second aqueous solution.

If desired, the second aqueous solution may be exchanged for another aqueous solution by washing, centrifugation, filtration, or removed by freeze-drying or lyophilization to form a solid dosage. The solid dosage form of the pharmaceutical composition obtained, by, for example freeze-drying, may be further processed to produce tablets, capsules, wafers, patches, suppositories, sutures, implants or other solid dosage forms known to those skilled in the art.

Pharmaceutical Composition

The pharmaceutical compositions of the invention comprise at least one type of biodegradable polymer or copolymer, at least one type of lipid and at least one physiologically active substance. The biodegradable polymer can take the form of a random copolymer or block copolymer, which can be made up of a variety of monomeric units. For example, if the biodegradable copolymer is made up of lactic acid (or lactide) and glycolic acid (or glycolide), the ratio of lactide to glycolide can range from about 99:1 to about 2:3, preferably from about 10:1 to about 1:1. The biodegradable polymer (in whatever form, homo- or co-polymer) and lipid can be present in a lipid to polymer ratio of from about 20:1 to about 1:5, preferably from about 19:1 to about 1:3.

The biodegradable polymer or copolymer and the lipid form a multicompartmental structure providing multiple non-concentric compartments for encapsulating hydrophilic physiologically active substances; the biodegradable polymer and the lipid forming the boundaries of the compartments. The boundaries can contain hydrophobic or amphipathic physiologically active substances. The pharmaceutical composition can be stored in a solid dosage form or semi-solid dosage form. The term "semi-solid dosage form" means an aqueous suspension of the pharmaceutical composition. A semi-solid dosage form can be formed by addition of an aqueous medium to a solid dosage form of the pharmaceutical composition, or can be formed directly by the double emulsion techniques described above. Preferred aqueous media are water, aqueous solutions of sodium chloride, pharmaceutical excipients, and buffered solutions with pH in the range 2 to 10. Preferred pharmaceutical excipients are phosphate, citrate, acetate, glucuronate, mannitol, polysorbate, carboxymethylcellulose, gelatin and lactate.

The term "solid dosage form" includes amorphous powders, tablets, capsules, aerosols, wafers, transdermal patches, suppositories, or implants. Amorphous powders can be formed by lyophilization of a semi-solid dosage form of the pharmaceutical composition. Tablets, capsules, aerosols, wafers, patches, suppositories, and implants can be formed by techniques well known to those in the art.

The pharmaceutical composition can be administered to a living being by any desired route, for example, intramuscular, intraarticular, epidural, intrathecal, intraperitoneal, subcutaneous, intravenous, intralymphatic, oral, submucosal, transdermal, rectal, vaginal, intranasal, intraocular and by implantation under different kinds of epithelia, including the bronchial epithelia, the gastrointestinal epithelia, the urogenital epithelia, and various mucous membranes of the body.

Characterization of the Pharmaceutical Composition

In order to compare the pharmaceutical compositions in their semi-solid suspension dosage forms, the following parameters are defined. The amount of the physiologically active substance in the suspension is determined by an appropriate assay as described below. The yield of the physiologically active substance is defined by the following equation.

$$\text{Yield (\%)} = \frac{\text{Amount Recovered (mg)}}{\text{Amount Input (mg)}} \cdot 100$$

In the above equation, the amount recovered is the amount of the physiologically active substance determined to be in the biodegradable microspheres of the pharmaceutical composition and the amount input is the total amount of the physiologically active substance used in the preparation of the pharmaceutical composition.

The suspension is centrifuged in hematocrit capillary tubes to produce a pellet fraction and a supernatant fraction. Using the standard technique of hematocrit measurement, the relative volumes of the pellet and of the suspension are given by the distance from the bottom of the pellet to the top of the pellet, and from the bottom of the pellet to the top of the supernatant, respectively. The ratio of the relative volume of the pellet and the relative volume of the suspension is defined as the pellet fraction and is given by the following equation.

$$\text{Pellet Fraction} = \frac{\text{Volume of the Pellet}}{\text{Volume of the Suspension}}$$

The unencapsulated fraction is defined as the fraction of the physiologically active substance in the pharmaceutical composition that is not encapsulated and resides outside of the biodegradable microspheres in the suspending medium, and is given by the following equation.

$$\text{Unencapsulated Fraction} = \frac{\text{Amount in the Supernatant (mg)}}{\text{Amount in the Suspension (mg)}}$$

The encapsulated fraction is one minus the unencapsulated fraction. Loading is defined as the concentration of the physiologically active substance in the pellet fraction of the suspension, and is given by the following equation.

$$\text{Loading (mg/mL)} = \frac{\text{Encapsulated Fraction}}{\text{Pellet Fraction}} \cdot \text{Concentration in Suspension (mg/mL)}.$$

The invention will be further described in the following examples, which do not limit the scope of the invention described in the claims.

EXAMPLES

The following examples illustrate the preparation and properties of the biodegradable lipid/polymer-containing pharmaceutical compositions of the present invention.

Example 1

Preparation of the Pharmaceutical Composition

The pharmaceutical compositions shown in Table 1 were prepared by the double emulsification process. The aqueous phase contained amikacin (Bristol-Myers Squibb, Syracuse, N.Y.) at the concentrations shown in Table 1 and a pH of 8. Additionally, for comparative formulations, the aqueous phase contained 4% polyvinyl alcohol (Sigma Chemical Co.) as indicated in Table 1.

The solvent phase contained either the polymer poly(DL-lactide-glycolide) (PLGA) alone at a concentration of 250 mg/mL, or a mixture of PLGA, diolcoyl phosphatidylcholine (DOPC), dipalmitoyl phosphatidylglycerol (DPPG), cholesterol and triolein at concentrations of 22.4 mg/mL, 10.4 mg/mL, 2.1 mg/mL, 7.7 mg/mL, and 2.2 mg/mL, respectively. PLGA was from Sigma Chemical Company (St. Louis, Mo.), with a lactide:glycolide ratio of 50:50 and a molecular weight of 40,000–75,000. This material (with lactide:glycolide of 1:1) was used in all experiments, except where indicated (in Example 4). DOPC, DPPG, and triolein were from Avanti Polar Lipids (Alabaster, Ala.), and cholesterol was from Spectrum Chemical Manufacturing Corp. (Gardena, Calif.). This corresponds to a solvent phase either with polymer alone, or with lipids and polymer in a 1:1 weight ratio. The ratios of the volume of the aqueous phase to the volume of the volatile organic solvent phase are given in Table 1. The "water-in-oil" emulsion was prepared by mixing on a Homo Mixer (Tokushu Kika Kogyo Co., Ltd., Osaka, Japan) at a speed of 9,600 rpm for 20 min. The second aqueous phase was either 4% wt. polyvinyl alcohol (PVA) for comparative formulations, water, or a mixture of 5% wt. glucose and 40 mM lysine. Spherules were formed by mixing at 4,000 rpm for 1 min. The suspending medium was exchanged with 0.9% wt. sodium chloride by washing and centrifuging at 600×g twice.

The concentration of amikacin in the pharmaceutical composition, and the supernatant of the pharmaceutical composition were determined by capillary electrophoresis (3D CE model 1600, Hewlett-Packard, Irvine, Calif.) using a fused silica column (50 µm inner diameter, 50 cm length, Hewlett-Packard, Irvine, Calif.), and 0.1 M phosphate, pH 2.5 (Peptide Separation Buffer, Sigma Chemical Co.) as the running buffer. The yield of the physiologically active substance and drug loading are summarized in Table 1.

The mean particle diameter was determined on a laser scattering particle size distribution analyzer (Model LA-910, Horiba Instruments, Irvine, Calif.) using the length-weighted distribution base and a relative refractive index of 1.18–1.00 i. The mean particle diameters were 43.6 μm for the polymer pharmaceutical composition prepared with 4 wt % polyvinyl alcohol (comparative formulation) in the second aqueous phase, and 9.0 μm for the lipid/polymer-containing pharmaceutical composition of the present invention in Table 1 with a lipid:polymer ratio of 1:1.

TABLE 1

Characteristics of Polymer-only and Lipid/Polymer-Containing Pharmaceutical Compositions.

| Aqueous Phase | | Solvent Phase | | Aqueous: Solvent Phase Volume Ratio (mL:mL) | Second Aqueous Phase | Yield (%) | Loading (mg/mL) |
|---|---|---|---|---|---|---|---|
| Amikacin, mg/mL | Excipients | Polymer | Lipids | | | | |
| 320 | None | PLGA | None | 5:0.5 | 4 wt % PVA | 31 | 20.8 |
| 320 | None | PLGA | None | 5:0.5 | H₂O | 0 | 0 |
| 320 | None | PLGA | None | 5:0.5 | 5 % Glucose, 40 mM Lysine | 0 | 0 |
| 80 | 4% PVA | PLGA | None | 5:5 | H₂O | 0 | 0 |
| 80 | 4% PVA | PLGA | None | 5:5 | 5% Glucose, 40 mM Lysine | 0 | 0 |
| 80 | None | PLGA | DOPC, DPPG, Cholesterol, Triolein | 5:5 | 5% Glucose, 40 mM Lysine | 64 | 65.9 |

The results in Table 1 show that addition of an emulsifier such as polyvinyl alcohol is required for the preparation of polymer-only microspheres containing physiologically active substance. They also show that addition of the emulsifier to the second aqueous phase is an absolute requirement for the encapsulation of physiologically active substance for polymer-only microspheres. The pharmaceutical composition of the present invention (last entry of Table 1) does not use such an emulsifier, in any of the aqueous phases. Instead, encapsulation is achieved by addition of lipids to the volatile organic solvent phase. Therefore, the lipid/polymer-containing pharmaceutical compositions of the present invention are quite different from the compositions of the prior art.

Additionally, Table 1 demonstrates the high loading which is achieved with the pharmaceutical compositions of the invention, even considering a four-fold lower concentration of pharmaceutically active composition in the first aqueous phase.

Example 2

Preparation of Pharmaceutical Compositions Containing Physiologically Active Substances.

The pharmaceutical compositions were prepared by employing a double emulsification process. The "water-in-oil" type emulsion was prepared from 5 mL of an aqueous phase containing the physiologically active substance and excipients the concentrations of which are specified in Table 2, and 5 mL of an volatile organic solvent phase, containing lipids and polymer at a ratio of 1:1 and was prepared as described in Example 1. The physiologically active substances were cytarabine (Pfanstiehl, Waukegan, Ill.), bovine zinc insulin (Sigma Chemical Co., St. Louis, Mo.), herring sperm DNA (Gibco BRL, Gaithersburg, Md.), or dexamethasone phosphate (Sigma Chemical Co., St. Louis, Mo.). The mixing speed and time for producing the "water-in-oil" type emulsion were 9,600 rpm for 20 min. The second aqueous phase was 30 ML of a solution containing 5% glucose and 40 mM lysine. Spherules were formed by mixing at 4,000 rpm for 1 min. The suspending medium was exchanged with 0.9% wt. sodium chloride by washing and centrifuging at 600×g twice.

The concentration of cytarabine in the pharmaceutical composition, and the supernatant of the pharmaceutical composition were determined by isocratic reverse phase HPLC (Hewlett-Packard, Wilmington, Del.) using a C18 column (Vydac, Hespena, Calif.), 10 mM potassium phosphate, pH 2.8 (J. T. Baker, Phillipsburg, N.J.) as the mobile phase, a flow rate of 1 mL/min and 280 nm for the wavelength of detection.

The concentration of insulin in the pharmaceutical composition, and the supernatant of the pharmaceutical composition were determined by isocratic reverse phase HPLC using a C18 column, a solution of 50% by volume of acetonitrile (Burdick & Jackson), 50% water and 0.1% trifluoroacetic acid (Pierce, Rockford, Ill.) as the mobile phase, a flow rate of 1 mL/min and 280 nm for the wavelength of detection.

The concentration of herring sperm DNA in the pharmaceutical composition, and the supernatant of the pharmaceutical composition were determined by measuring absorbance at 260 nm on a spectrophotometer (Model U-2000, Hitachi, Danbury, Conn.) of the pharmaceutical composition dissolved in acidic isopropanol relative to that of a standard solution of herring sperm DNA of known concentration.

The concentration of dexamethasone in the pharmaceutical composition, and the supernatant of the pharmaceutical composition were determined by isocratic reverse phase HPLC using a C18 column (5 µm, 4.6×250 mm, Vydac), a mixture of 60% by volume methanol and 40% of 50 mM potassium phosphate, pH 2.8 as the mobile phase, a flow rate of 0.5 mL/min and 254 nm for the wavelength of detection.

The yield of the physiologically active substance, drug loading and the mean particle diameter are summarized in Table 2.

TABLE 2

Characteristics of Pharmaceutical Compositions containing Physiologically Active Compounds

| Physiologically Active Substance | Aqueous Phase Concentration (mg/mL) | Excipients | Yield (%) | Mean Particle Diameter (µm) | Drug Loading (mg/mL) |
| --- | --- | --- | --- | --- | --- |
| Cytarabine | 30 | 136 mM HCl | 70 | 17 | 25.0 |
| Cytarabine | 75 | None | 62 | 14 | 59.6 |
| Insulin | 20 | 5% Dextrose, 50 mM HCl | 38 | 13 | 10.7 |
| Herring Sperm DNA | 1 | None | 45 | 14 | 0.16 |
| Dexamethasone phosphate | 15 | None | 14 | 7 | 13.4 |

Example 3

Preparation of Pharmaceutical Compositions with Different Lipid:polymer Ratios

The pharmaceutical compositions were prepared as described in Example 2, with the following modifications. The aqueous phase contained either 30 mg/mL cytarabine and 136 mM hydrochloric acid, or 20 mg/mL bovine zinc insulin, 5% dextrose and 50 mM hydrochloric acid. A series of volatile organic solvent phases with lipid:polymer ratios of 1:0, 19:1, 4:1, 3:2, 1:1 or 1:3 were prepared by mixing in varying proportions a chloroform solution containing dioleoyl phosphatidylcholine, cholesterol, dipalmitoyl phosphatidylglycerol, and triolein at concentrations of 20.8 mg/mL, 15.4 mg/mL, 4.2 mg/mL and 4.4 mg/mL, respectively, with a chloroform solution of the polymer at a concentration of 44.8 mg/mL. In Table 3, the first aqueous solution was a mixture of 30 mg/mL cytarabine and 136 mM hydrochloric acid. In Table 4, the first aqueous solution was a mixture of 20 mg/mL insulin, 50 mM hydrochloric acid and 5 wt % dextrose. The concentrations of cytarabine and insulin were determined by assays as described in Example 2.

The yield, mean particle diameter and drug loading for the pharmaceutical compositions containing cytarabine are given in Table 3, and the characteristics for the pharmaceutical compositions containing insulin are in Table 4.

TABLE 3

Characteristics of Cytarabine-containing Pharmaceutical Compositions Containing Differing Lipid-Polymer Ratios.

| Lipid:Polymer | Yield (%) | Mean Particle Diameter, µm | Drug Loading (mg/mL) |
| --- | --- | --- | --- |
| 1:0 | 56 | 15 | 43.5 |
| 19:1 | 58 | 13 | 34.6 |
| 4:1 | 78 | 11 | 35.5 |
| 3:2 | 80 | 14 | 34.1 |
| 1:3 | 31 | 15 | 21.7 |

TABLE 4

Characteristics of Insulin-containing Pharmaceutical Compositions Containing Differing Lipid-Polymer Ratios.

| Lipid:Polymer | Yield (%) | Mean Particle Diameter, µm | Drug Loading (mg/mL) |
| --- | --- | --- | --- |
| 1:0 | 68 | 17 | 29.4 |
| 4:1 | 100 | 16 | 22.5 |
| 3:2 | 83 | 14 | 21.8 |
| 1:1 | 38 | 13 | 10.7 |

As the results in Tables 3 and 4 demonstrate, high yields of physiologically active substances are generally achieved through use of the lipid/polymer-containing compositions of the invention. The mean particle diameters are typically between 5 and 25 µm, and are usually between 10 and 20 µm.

Example 4

Preparation of Pharmaceutical Compositions with Differing Lipid:Polymer Ratios and with Polymers of Differing Molecular Weight and Differing Lactide:Glycolide The pharmaceutical compositions were prepared by employing a double emulsification process. The "water-in-oil" type emulsion was prepared from an aqueous phase containing the physiologically active substance cytarabine at a concentration of 30 mg/mL in 136 mM hydrochloric acid, and an volatile organic solvent phase containing dioleoyl phosphatidylcholine, cholesterol, dipalmitoyl phosphatidylglyerol, triolein, and a poly (lactide-glycolide) polymer (Alkermes, Inc., Blue Ash, Ohio), as presented in Example 3. The yields of the physiologically active substance, mean particle diameter and drug loading for the pharmaceutical composition with polymers of different lactide:glycolide ratios and varying lipid:polymer ratios are summarized in Tables 5, 6 and 7, respectively.

TABLE 5

Yield of Physiologically Active Substance Obtained with Differing Molecular Weight and Lactide:Glycolide.

| Lactide:Glycolide Ratio | Polymer Molecular Weight | Yield (%) at Different Lipid:Polymer Ratios | | | |
| --- | --- | --- | --- | --- | --- |
| | | 4:1 | 3:2 | 1:1 | 0:1 |
| 100:0 | 128,450 | 50 | 54 | 56 | 0 |
| 85:15 | 149,000 | 55 | 56 | 51 | 0 |
| 75:25 | 130,132 | 43 | 58 | 60 | 0 |
| 65:35 | 141,000 | 49 | 50 | 55 | 2 |
| 50:50 | 69,587 | 51 | 63 | 54 | 2 |

TABLE 6

Mean Particle Diameter of Pharmaceutical Compositions Obtained with Differing Molecular Weight and Lactide:Glycolide.

| Lactide:Glycolide Ratio | Polymer Molecular Weight | Mean Particle Diameter (μm) at Different Lipid:Polymer Ratios | | | |
|---|---|---|---|---|---|
| | | 4:1 | 3:2 | 1:1 | 0:1 |
| 100:0 | 128,450 | 12 | 11 | 11 | ND |
| 85:15 | 149,000 | 12 | 11 | 11 | 4 |
| 75:25 | 130,132 | 15 | 11 | 11 | ND |
| 65:35 | 141,000 | 12 | 10 | 10 | 77 |
| 50:50 | 69,587 | 11 | 10 | 11 | 5 |

ND - Not Determined

TABLE 7

Loading of Physiologically Active Substance Into Pharmaceutical Compositions Obtained with Differing Molecular Weight and Lactide:Glycolide.

| Lactide:Glycolide Ratio | Polymer Molecular Weight | Loading in the Pharmaceutical Composition (mg/mL) at Different Lipid:Polymer Ratios | | | |
|---|---|---|---|---|---|
| | | 4:1 | 3:2 | 1:1 | 0:1 |
| 100:0 | 128,450 | 44.9 | 43.0 | 38.6 | 0 |
| 85:15 | 149,000 | 46.9 | 47.0 | 40.0 | 0 |
| 75:25 | 130,132 | 45.2 | 46.7 | 32.8 | 0 |
| 65:35 | 141,000 | 46.2 | 41.0 | 34.7 | 4.5 |
| 50:50 | 69,587 | 42.0 | 45.5 | 38.7 | 7.7 |

The results in Tables 5, 6 and 7 demonstrate that the inventive pharmaceutical compositions display generally high yields and uniform loading of physiologically active substance regardless of the lactide:glycolide ratio, molecular weight of biodegradable polymer, or lipid:polymer ratio, as long as some lipid is present in the compositions. The pharmaceutical compositions of the invention have remarkably similar mean particle diameters, all generally falling between 5 and 25 μm, and usually between 10 and 20 μm.

Example 5

Pharmaceutical Composition Containing a Hydrophobic Physiologically Active Substance with and without a Triglyceride Two pharmaceutical compositions, one with triglyceride and another without triglyceride, were prepared as generally described in Example 2 with the following modifications. The hydrophobic physiologically active substance was paclitaxel. For the composition with triglyceride, the chloroform solution contained poly(lactide-glycolide), DOPC, DPPG, cholesterol, and triolein (the triglyceride) at concentrations given in Example 2, and paclitaxel (ICN Biochemicals, Aurora, Ohio) at a concentration of 5 mg/mL. For the composition without triglyceride, the chloroform solution contained poly(lactide-glycolide), DOPC, DPPG and cholesterol at the concentrations given in Example 2 and paclitaxel at a concentration of 5 mg/mL. For both compositions, the lipid:polymer ratio was 1:1. For both compositions, 5 mL of an aqueous solution containing 10% wt. sucrose (Pfanstiehl, Waukegan, Ill.) was used to prepare the "water-in-oil" type emulsion.

The concentration of paclitaxel in the pharmaceutical compositions was determined by reverse phase HPLC with a C18 column (5 μm, 4.6×250 mm, 90 A, Vydac), a water (Mallinckrodt, Paris, Ky.):acetonitrile gradient with a flow rate of 1 mL/min and using 273 nm as the wavelength of detection. Yield, particle size and drug loading for both compositions are shown in Table 8.

TABLE 8

Characteristics of Pharmaceutical Compositions Containing Paclitaxel in the Presence and Absence of Triglyceride.

| Composition | Yield (%) | Mean Particle Diameter (μm) | Drug Loading (mg/mL) |
|---|---|---|---|
| With Triglyceride | 52 | 16 | 4.0 |
| Without Triglyceride | 53 | 16 | 12.1 |

This example shows that significantly higher loading of hydrophobic physiologically active substances is obtained when a triglyceride is omitted from the composition.

Example 6

Pharmaceutical Composition Containing a Hydrophilic Physiologically Active Substance with and without a Triglyceride Two pharmaceutical compositions, one with triglyceride and another without triglyceride, were prepared as generally described in Example 2 with the following modifications. The hydrophilic physiologically active substance was amikacin. For the composition with triglyceride, the chloroform solution contained poly(lactide-glycolide), DOPC, DPPG, cholesterol, and triolein (the triglyceride) at concentrations given in Example 2. For the composition without triglyceride, the chloroform solution contained poly(lactide-glycolide), DOPC, DPPG and cholesterol at the concentrations given in Example 2. For both compositions, the lipid:polymer ratio was 1:1. For both compositions, 5 mL of an aqueous solution containing 80 mg/mL amikacin, pH 8 was used to prepare the water-in-oil emulsion. Yield, particle size and drug loading for both compositions are shown in Table 9.

TABLE 9

Characteristics of pharmaceutical compositions containing amikacin in the presence and absence of a triglyceride.

| Composition | Yield (%) | Mean Particle Diameter (μm) | Drug Loading (mg/mL) |
|---|---|---|---|
| With Triglyceride | 64 | 9 | 65.9 |
| Without Triglyceride | 0 | 4 | 0 |

This example shows that loading of hydrophilic physiologically active substances does not occur when a triglyceride is excluded from the composition. In contrast significant loading of hydrophilic physiologically active substances occurs with triglyceride present in the composition.

Example 7

Sustained Release in vitro of Encapsulated Physiologically Active Substance from Pharmaceutical Composition In vitro release studies were performed in human plasma under static and dynamic conditions. Two sets of pharmaceutical compositions for in vitro release studies were prepared as described in Example 2 with the following modifications. One set was prepared from an aqueous phase containing 30 mg/mL cytarabine in 136 mM hydrochloric acid. Another set was prepared from an aqueous phase containing 75 mg/mL cytarabine in water. For each set, three compositions were prepared as described in Example 3 with lipid:polymer ratios of 4:1, 3:2 and 1:1. For all six pharmaceutical compositions, the concentration of cytarabine was adjusted to 10 mg/mL. The pharmaceutical composition (1 mL) was mixed with type O human plasma (24 mL) (NABI Biomedical, Scottsdale, Ariz.) and 1% wt. sodium azide (150 µL) (Sigma Chemical Co., St Louis, Mo.).

For the in vitro release studies under static conditions, aliquots of 1.5 mL in triplicate were placed in vials which were incubated at 37° C. for different time periods extending up to 14 days. For the in vitro release studies under dynamic conditions, the vials were placed on a rotator (Hematology/Chemistry Mixer, Model 346, Fisher Scientific, Pittsburgh, Pa.) continuously rotating at 16 rpm. The platform was placed in an incubator at 37° C. for different time periods extending up to 14 days.

At each time point, 10 µL of 0.9% sodium chloride were added to an aliquot and the resulting suspension was centrifuged for 10 min. at 600×g. The supernatants were discarded and the pellets were solubilized in a solution of 12:3:1 acetonitrile:isopropyl alcohol:1N hydrochloric acid. The amount of the physiologically active substance in the solubilized pellet was determined as described in the assay for cytarabine (see Example 2). The percentage encapsulated drug in FIGS. 1, 2, 3 and 4 is defined by the following equation.

$$\text{Encapsulated Drug (\%)} = \frac{\text{Amount in the Pellet (mg)}}{\text{Amount in the Pellet at Time Zero (mg)}} \cdot 100.$$

Figure 2:
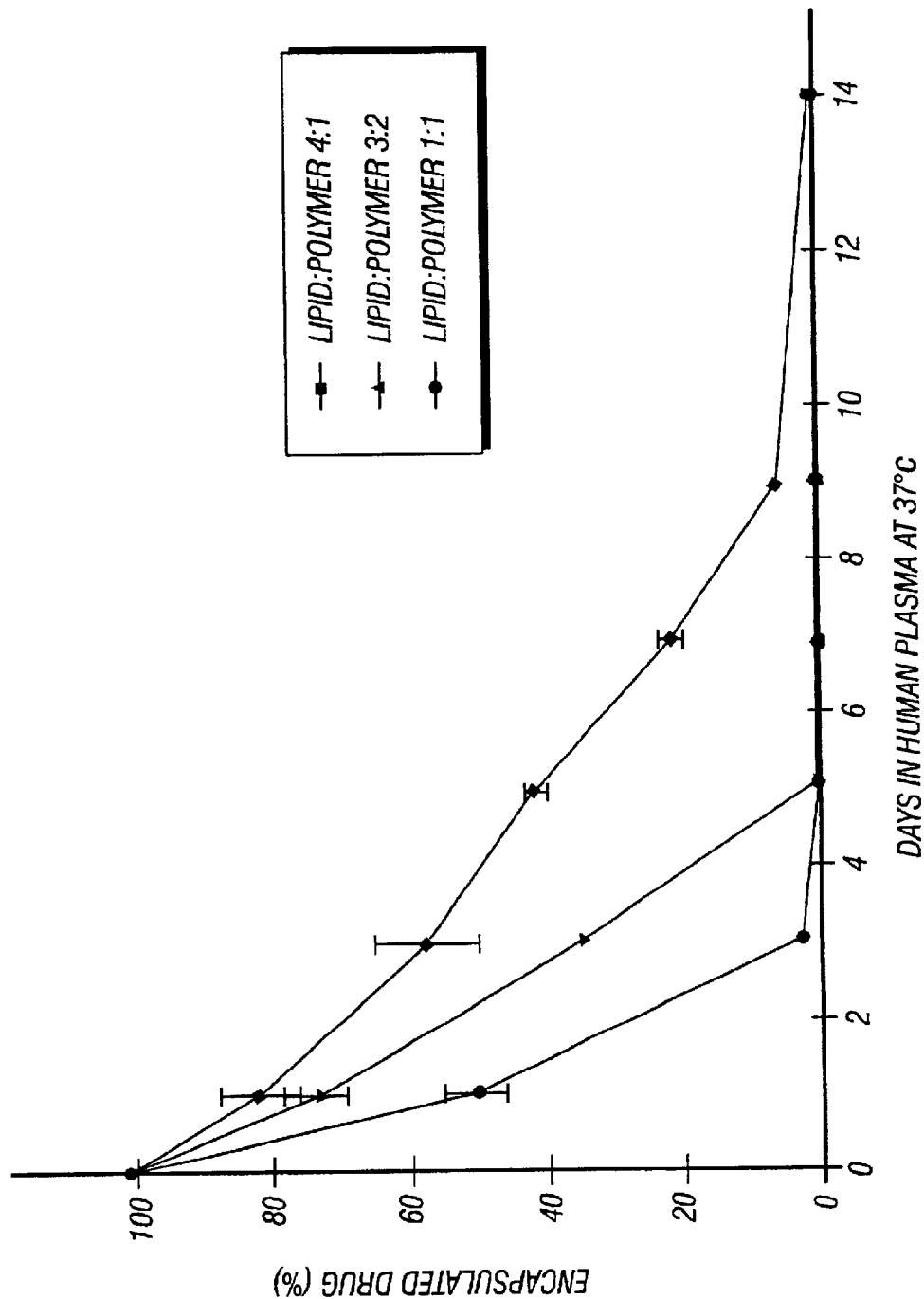
FIG. 2 is a plot of the percentage of encapsulated cytarabine from various lipid/polymer-containing pharmaceutical compositions prepared from cytarabine in water under static conditions versus time in vitro.
Figure 3:
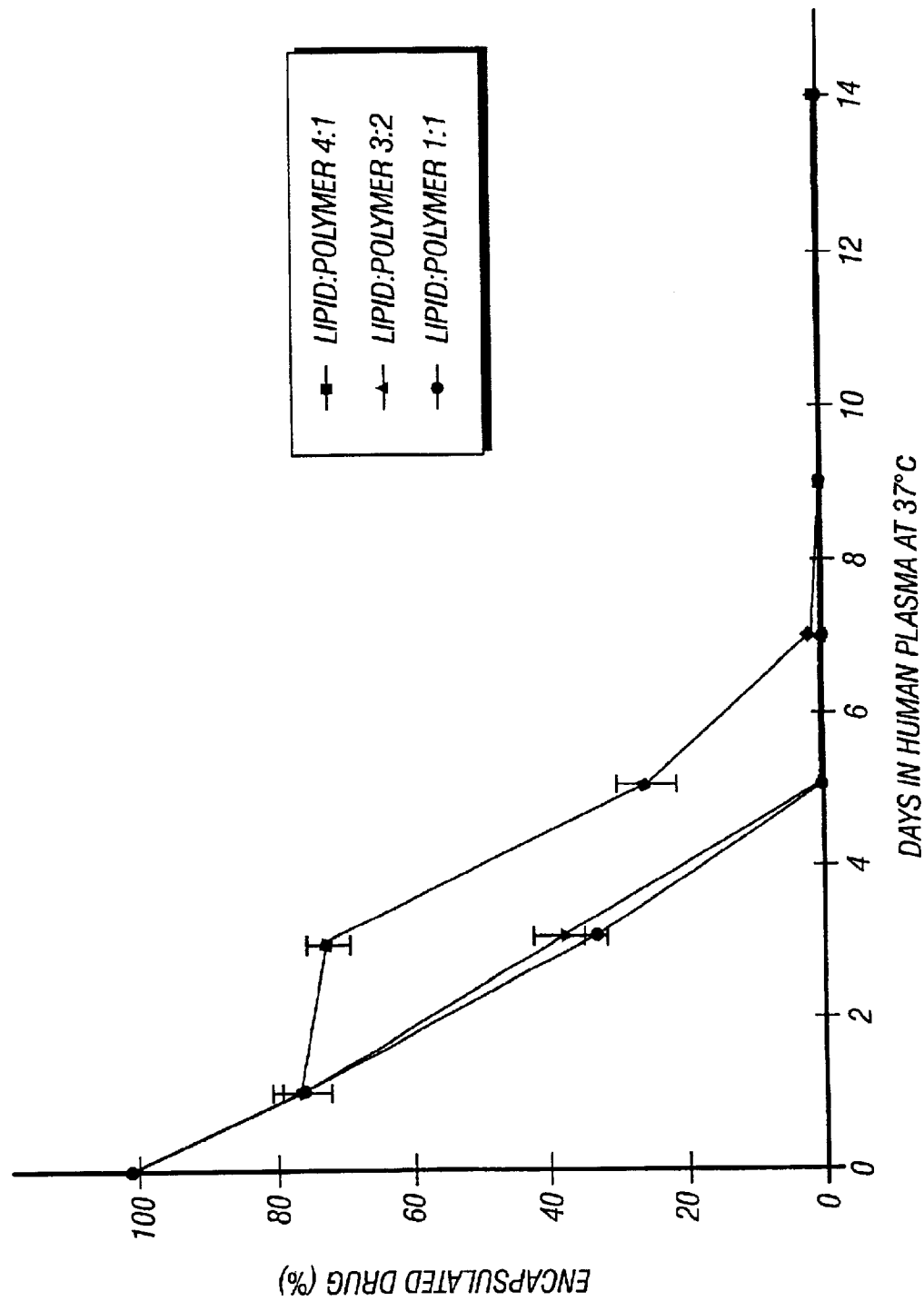
FIG. 3 is a plot of the percentage of encapsulated cytarabine from various lipid/polymer-containing pharmaceutical compositions prepared from cytarabine in hydrochloric acid under dynamic conditions versus time in vitro.
Figure 4:
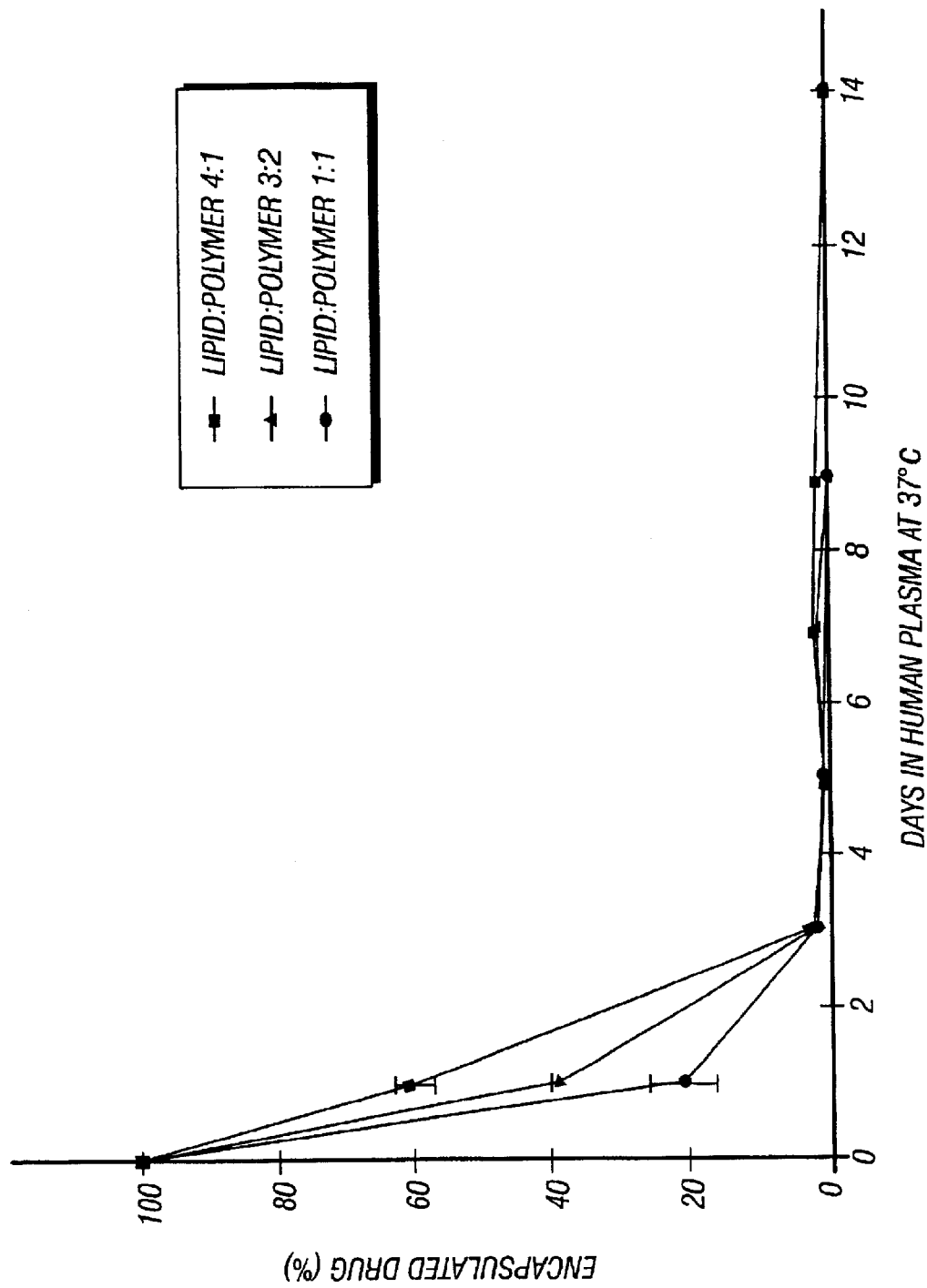
FIG. 4 is a plot of the percentage of encapsulated cytarabine from various lipid/polymer-containing pharmaceutical compositions prepared from cytarabine in water under dynamic conditions versus time in vitro.

The in vitro release profiles in plasma for the lipid/polymer-containing pharmaceutical compositions of lipid-:polymer ratios 4:1, 3:2 and 1:1 with 30 mg/mL cytarabine in 136 mM hydrochloric acid under static conditions for the in vitro release assay are shown in FIG. 1. The corresponding release profiles for the 4:1, 3:2 and 1:1 lipid/polymer-containing pharmaceutical compositions containing 75 mg/mL cytarabine in water obtained under static conditions are shown in FIG. 2. The release profiles for the lipid/polymer-containing pharmaceutical compositions measured under dynamic conditions are shown in FIGS. 3 (30 mg.mL cytarabine in 136 mM hydrochloric acid) and 4 (75 mg/mL cytarabine in water).

These data show that sustained release of the encapsulated physiologically active substance into physiological media is obtained for both compositions under different assay conditions. They also show that the sustained release can be controlled by varying the lipid:polymer ratio.

Example 8

Sustained Release in vivo of Encapsulated Physiologically Active Substance from Pharmaceutical Composition after a Single Oral Administration A lipid-only pharmaceutical composition and a lipid/polymer-containing pharmaceutical composition with lipid-:polymer ratio 1:1 were prepared as in Example 1 with the following modifications. The aqueous solution contained 80 mg/mL amikacin, pH 8. For preparing the lipid/polymer-containing pharmaceutical composition with lipid to polymer ratio of 1:1 by weight, the chloroform solution was as described in Example 2. For the lipid-only pharmaceutical composition, the chloroform solution contained DOPC, DPPG, cholesterol and triolein at the concentrations specified in Example 2, without the polymer. The mean particle diameters for the polymer-only and the 1:1 lipid/polymer-containing pharmaceutical compositions with a lipid to polymer ratio of 1:1 by weight were 8.4 and 7.8 µm, respectively.

For preparation of the polymer-only pharmaceutical composition, 5 mL of a chloroform solution containing poly(lactide-glycolide) at a concentration of 250 mg/mL, and 0.5 mL of an aqueous solution containing 320 mg/mL amikacin, pH 8 were used. The second emulsion was formed by the addition of 20 mL of a 4% polyvinyl alcohol, and mixing at 4000 rpm for 1 minute. The contents of the mixing vessel were poured into a 1 liter Erlenmeyer flask containing 30 mL 4% polyvinyl alcohol. A stream of nitrogen gas set at 50 psi for 20 minutes at 37° C. was flushed through the flask to evaporate the chloroform. The mean particle diameter for the polymer pharmaceutical composition was 42.1 µm.

The lipid-only, 1:1 lipid/polymer and the polymer-only pharmaceutical compositions with amikacin encapsulated therein, or unencapsulated amikacin as a solution at pH 8 was administered orally by gavage to 300 g male Harlan Sprague Dawley albino rats. The number of animals per group was six. The dose was 20 mg per rat and the volume was 2 mL. Serum was collected via venipuncture (saphenous vein) from unanesthetized animals at 15, 45, 90 min., 3, 8, 24, and 48 hours. The specimens were kept at −40° C. until analysis.

The concentration of amikacin in serum was determined using a competitive particle concentration fluorescence immunoassay. Polystyrene beads (Idexx Research Product Division, Memphis, Tenn.) were first coated with anti-amikacin antibody (The Binding Site, San Diego, Calif.). The beads were incubated with a combination of fluorescent-labeled amikacin (The Binding Site) and serum containing amikacin which compete for the anti-amikacin antibody sites on the beads. The amount of fluorescent-labeled amikacin bound to the beads was measured by a fluorescence concentration analyzer (Idexx Research Product Division) which is inversely proportional to the amikacin concentration in serum.

Figure 5:
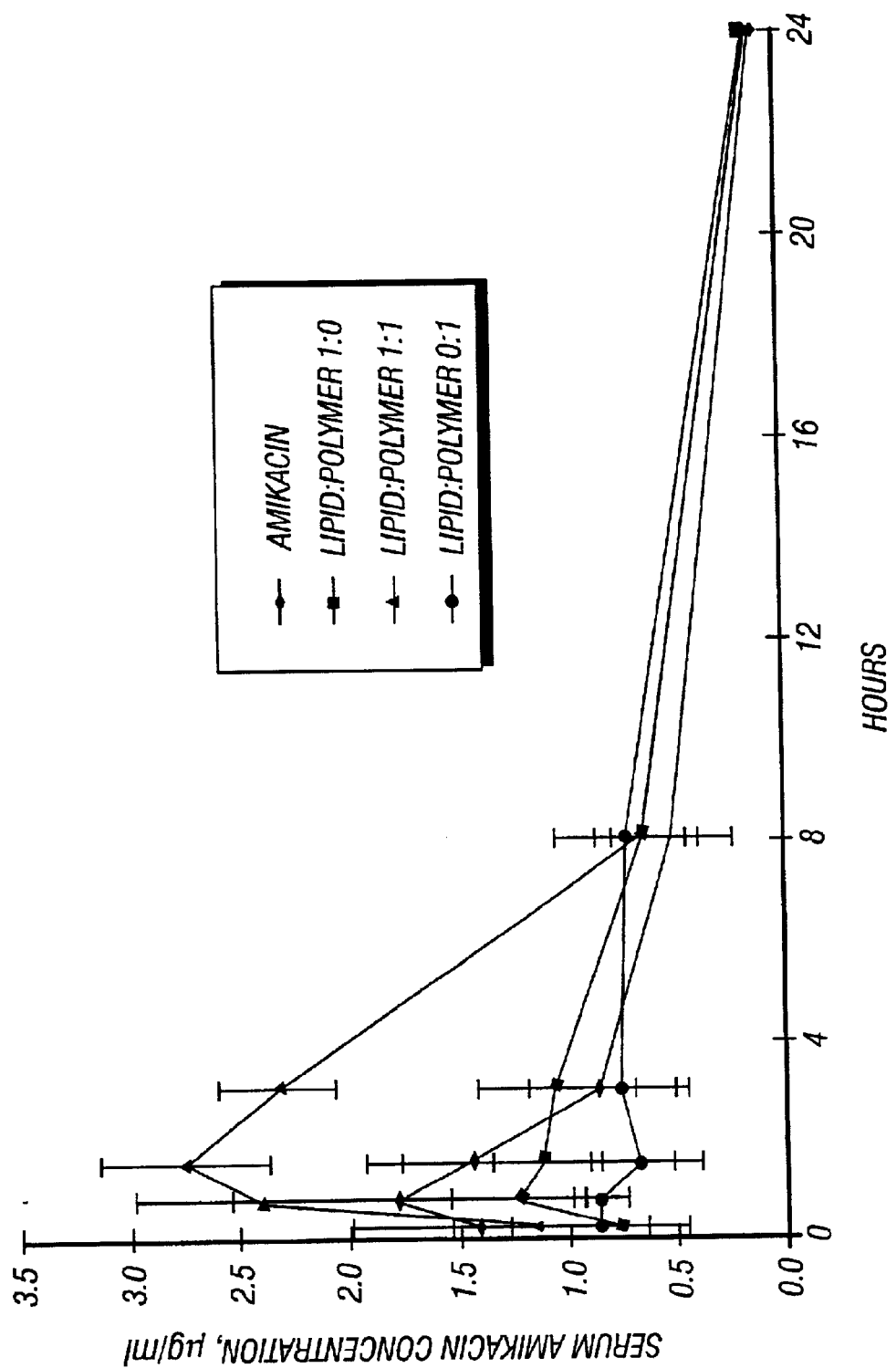
FIG. 5 is a plot of the serum concentrations of amikacin at different times after oral administration of unencapsulated amikacin, amikacin encapsulated into a lipid-only pharmaceutical composition, a lipid/polymer-containing pharmaceutical composition with lipid:polymer ratio of 1:1, or a polymer-only pharmaceutical composition.

The concentration of amikacin (µg/mL) in serum at different time points after oral administration for the four treatment groups is shown in FIG. 5. As seen in this figure, the peak circulatory levels were reached at 45 minutes for unencapsulated amikacin, the lipid, and the polymer pharmaceutical compositions, while for the 1:1 lipid/polymer-containing pharmaceutical composition, the peak level was prolonged to 90 minutes. This result demonstrates that use of the lipid/polymer-containing pharmaceutical composition results in a longer duration of release for the encapsulated physiologically active substance. Further, the concentration of amikacin in circulation reached peak levels of 1.82±0.73, 1.25±0.32 and 0.87±0.13 µg/mL for unencapsulated amikacin, the lipid, and the polymer pharmaceutical compositions respectively, while for the 1:1 lipid/polymer-containing pharmaceutical composition, a much greater peak level of 2.77±0.39 µg/mL was obtained. This result shows that the bioavailability of the physiologically active substance is enhanced by use of the lipid/polymer-containing pharmaceutical composition.

Example 9

Stability of Polymers upon Storage in Aqueous Medium

The effect of exposure to an aqueous environment, accelerated by heat and acid on the molecular weight of the polymer, poly(lactide-glycolide), alone or when it is present in the lipid/polymer-containing composition, was determined by size exclusion chromatography. A lipid/polymer-containing pharmaceutical composition with a lipid:polymer ratio of 1:1 by weight and cytarabine as the physiologically active substance was prepared as described in Example 3. The pellet fraction was adjusted to be 0.2. The suspending medium was 0.9% sodium chloride.

The average molecular weight of the polymer was determined by size exclusion chromatography using an evaporative light scattering detector (Richard Scientific, Laurel, Md.), two serially coupled gel filtration columns (Phenogel $10^3$ and $10^4$ A, 7.8×300 mm, Phenomenex, Torrance, Calif.), and chloroform as the mobile phase at a flow rate of 1 mL/min. The calibration curve was generated using 1 mg/mL chloroform solutions of polystyrene standards of molecular weight 12600, 20800, 37400, 53500, 79000, and 95050 (American Polymer Standards Corporation, Mentor, Ohio). The average molecular weight was calculated following standard procedures: Standard test method for molecular weight averages and molecular weight distribution by liquid exclusion chromatography (GEL permeation chromatography—GPC) (American Society for Testing and materials. D 3536-91. Pp. 352–362. 1992; Standard test method for molecular weight averages and molecular weight distribution of polystyrene by high performance size-exclusion chromatography. American Society for Testing and Materials. D 5296-92. Pp. 1–14. 1992).

Figure 6:
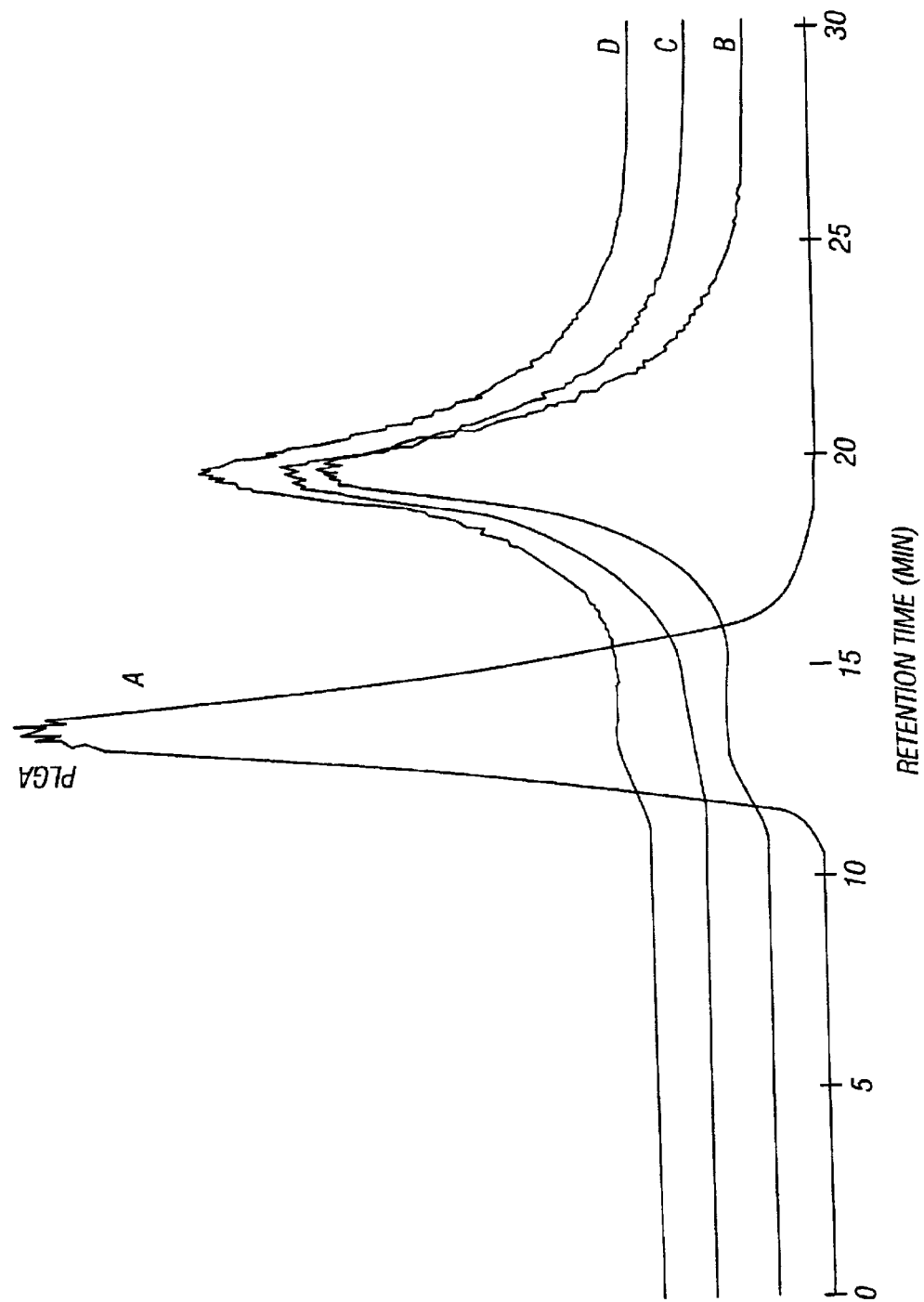
FIG. 6 is a series of size exclusion chromatograms of (A) a solution of polymer-only composition in chloroform, (B) polymer-only composition suspended in sodium chloride, (C) polymer-only composition suspended in hydrochloric acid, and (D) polymer-only composition suspended in hydrochloric acid and heat-stressed.

For the polymer-only control composition, a 2 mg/mL solution of poly(lactide-glycolide) in chloroform was prepared. Samples for determining the effect of exposure to an aqueous medium, and for acid and heat stress studies were prepared as follows. A 1 mg/mL solution of the polymer was dried in a vacuum desiccator in order to form a dry residue in a glass vial. Normal saline (750 µL of 0.9% sodium chloride) was added to the glass vial. This sample was used to determine the effect of exposure to an aqueous medium on polymer stability. To determine the effect of acid, 1 mg of the dry residue of the polymer formed in a glass vial was dispersed in 750 µL of 1 N hydrochloric acid and incubated for 1 hour. To determine the effect of acid and heat, 1 mg of the dry residue formed in a glass vial was dispersed in 750 µL of 1 N hydrochloric acid and placed in a boiling water bath for 1 hour. After the samples were incubated as described above, the polymer was extracted by adding 750 µL of chloroform. The chloroform layer was dried in a vacuum desiccator. The dry residue was taken up into chloroform to give a concentration of 2 mg/mL for size exclusion chromatography. Size exclusion chromatograms of a solution of the polymer in chloroform (curve A), the polymer suspended in saline (curve B), the suspension of the polymer suspended in 1 N hydrochloric acid (curve C), and the suspension of the polymer in 1 N hydrochloric acid further stressed by heat (curve D) are shown in FIG. 6. As seen in FIG. 6, the retention time of the polymer is increased upon addition of saline, or when the polymer is subjected to heat or acid, indicating a degradation of the polymer into smaller molecular weight fragments.

Figure 7:
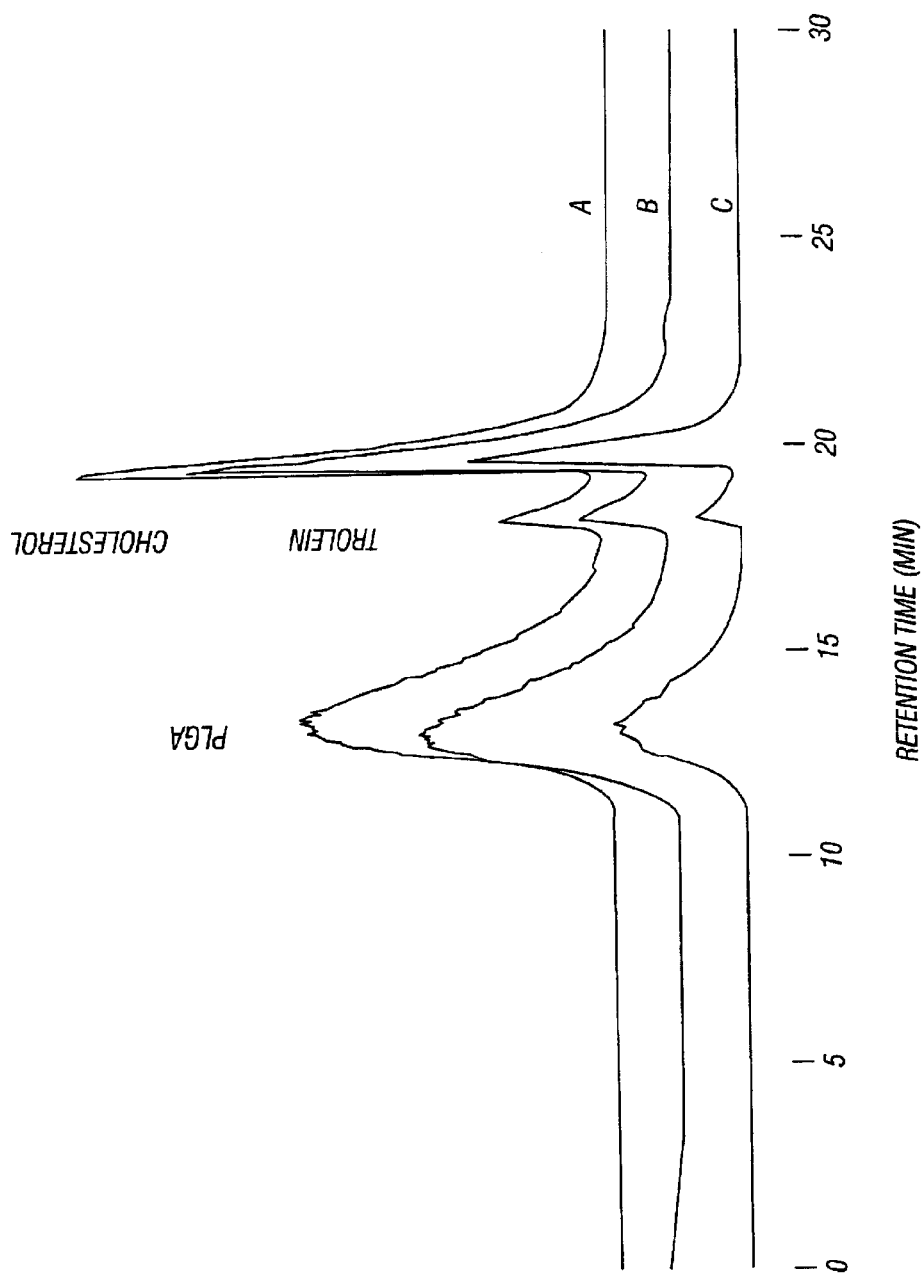
FIG. 7 is a series of size exclusion chromatograms of a suspension of lipid/polymer-containing pharmaceutical compositions with lipid:polymer ratios of 1:1 by weight (A) stored in sodium chloride, (B) stored in hydrochloric acid, (C) stored in hydrochloric acid and heat-stressed.

In order to determine the degradation of the polymer when it is present in the lipid/polymer-containing compositions of the present invention under acid and heat stressed conditions, 10 mL of a lipid/polymer-containing pharmaceutical composition with lipid to polymer ratio of 1:1 by weight containing cytarabine prepared as described in Example 2 with a pellet fraction of 0.2, suspended in 0.9% sodium chloride, were centrifuged at 600×g. To determine the effect of acid, most of the supernatant (7.5 mL) was discarded and replaced with 7.5 mL of 1 N hydrochloric acid and incubated at ambient temperature for 1 hr. To determine the effect of acid and heat, the suspension in 1 N hydrochloric acid was heated in a boiling water bath for 1 hr. Size exclusion chromatograms of the unstressed sample stored as a suspension in 0.9% sodium chloride (curve A), the sample stressed by acid (curve B), and the sample stressed by acid and heat (curve C) are shown in FIG. 7. As seen in FIG. 7, the retention time of the polymer is largely unaffected upon adding acid, or heat, indicating that the polymer is protected against hydrolysis by the presence of the lipid in the pharmaceutical compositions.

Figure 8:
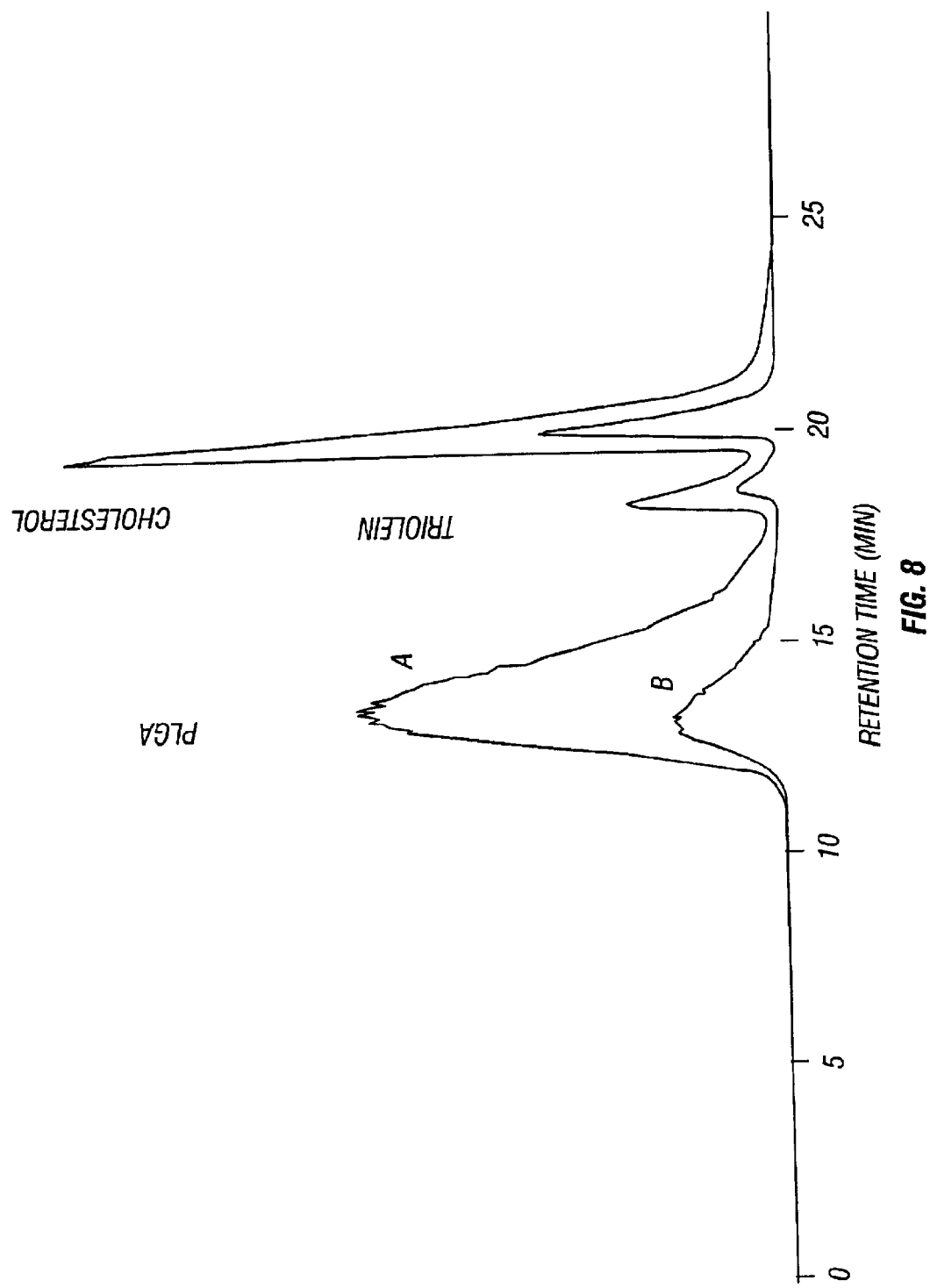
FIG. 8 is a series of size exclusion chromatograms of a suspension of (A) a freshly prepared lipid/polymer-containing pharmaceutical composition with lipid:polymer ratio of 1:1 by weight, and (B) an identical sample stored in the refrigerator for 9 months.

In order to determine polymer degradation under normal storage conditions, a lipid/polymer-containing pharmaceutical composition with a 1:1 lipid:polymer ratio by weight and cytarabine as the physiologically active substance was prepared as described in Example 2. The pharmaceutical composition was stored as a suspension in 0.9% sodium chloride in a refrigerator (2–8° C.) for 9 months. The size exclusion chromatograms of a freshly prepared lipid/polymer-containing pharmaceutical composition (curve A) and of a 9 month old composition (curve B) are shown in FIG. 8. As seen in FIG. 8, the polymer has not undergone significant hydrolysis during normal storage conditions.

Another accelerated stability study was conducted in order to compare the change in molecular weight of the polymer as a function of time of incubation at 37° C. for a lipid/polymer-containing pharmaceutical composition with lipid to polymer ratio of 1:1 by weight and a polymer-only formulation with no lipid. The lipid/polymer-containing pharmaceutical composition contained a physiologically active substance, cytarabine, and was prepared as described in Example 3. The polymer-only formulation also contained cytarabine and was prepared as described in Example 8, except that the first aqueous medium contained 150 mg/mL cytarabine in water. The average molecular weight of each polymer at different times of incubation at 37° C. was calculated as described above.

Figure 9:
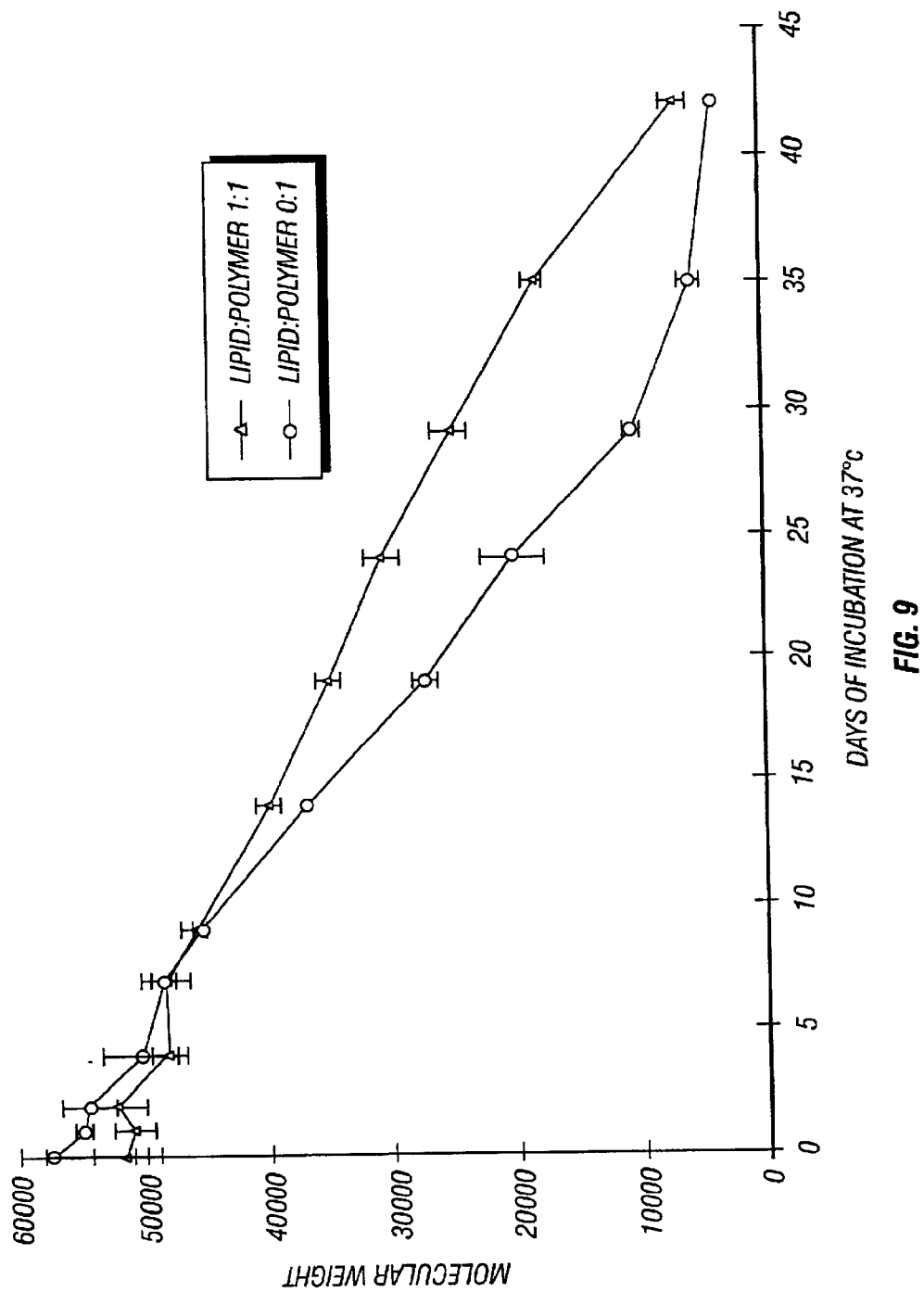
FIG. 9 is a plot of the change in molecular weight of PLGA in a lipid/polymer-containing pharmaceutical composition with lipid:polymer ratio of 1:1 by weight ($\Delta$) and a polymer-only pharmaceutical composition (O) versus time.

The results of this study, shown in FIG. 9 as circles for the polymer-only pharmaceutical composition and as triangles for the 1:1 lipid/polymer-containing pharmaceutical composition of the present invention, indicate that the rate of polymer degradation is slower for the lipid/polymer-containing pharmaceutical composition than for the polymer-only pharmaceutical composition.

Example 10

Osmotic Sensitivity of Pharmaceutical Composition

A polymer-only pharmaceutical composition and a lipid/polymer-containing pharmaceutical composition with lipid-polymer ratio, 9:1, 1:1, or 1:3 were prepared as in Example 1 and Example 8. For preparing the lipid/polymer-containing pharmaceutical composition with lipid to polymer ratio of 9:1, 1:1, and 1:3 by weight, the choloroform solution was as described in Example 2.

Sodium Chloride (Fisher Scientific) was added to water in varying amounts which resulted in solutions with the following osmolalities: 57, 116, 180, 269, 341, 422 mOsm/kg. The lipid/polymer containing pharmaceutical composition with lipid-polymer ratio 9:1, 1:1, and 1:3 or the polymer-only pharmaceutical composition were added into each one of the sodium chloride solutions. The particle diameters were measured using a laser scattering particle size distribution analyzer (Model LA-910, Horiba Instruments, Irvine, Calif.) using the length weighted distribution base and a relative refractive index of 1.18–1.00 i. The mean particle diameters as a function of osmolality are shown in FIG. 10.

Figure 10:
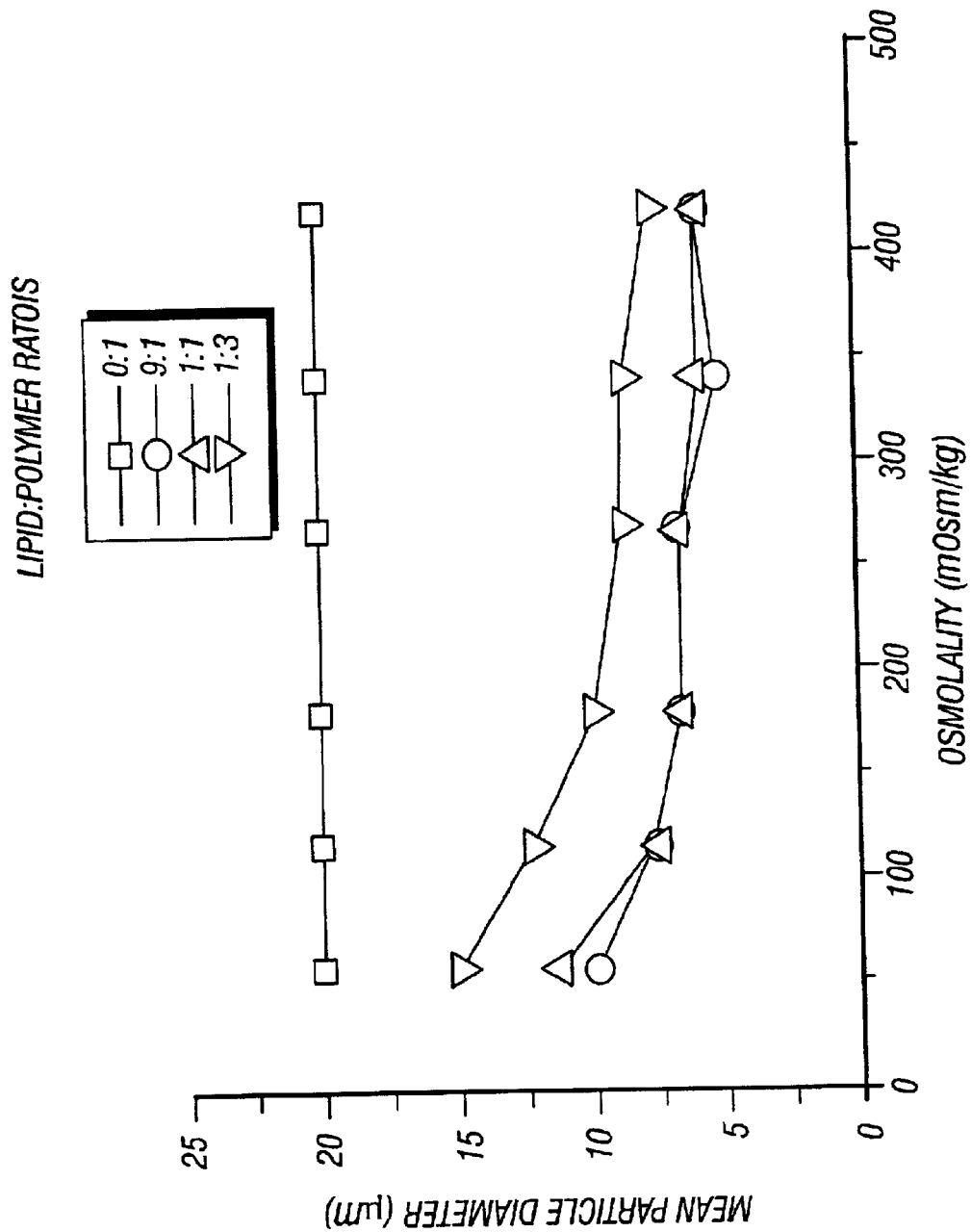
FIG. 10 is a plot of the change in mean particle diameter with the osmolality of the suspending medium for lipid/polymer microspheres of various compositions.

FIG. 10 shows that the size of the lipid/polymer mcirosphere compositions shows a dependence on the osmolality of the suspending medium. The size of polymer-only microsphere is independent of osmotic stress under these conditions, however.

Example 11

Sustained Release in vivo of Encapsulated Physiologically Active Substance from Pharmaceutical Composition after Subcutaneous Administration A lipid/polymer-containing pharmaceutical composition with lipid:polymer ratio 1.9:1 was prepared as in Example 1 with the following modifications. The aqueous solution contained 15 mg/mL leuprolide. For preparing the lipid/polymer-containing pharmaceutical composition with lipid to polymer ratio of 1.9:1 by weight. The chloroform solution is as described in Example 2. The chloroform solution contained the polymer poly(DL-lactide) (PLA) at a concentration of 37.22 mg/mL, DEPC, DPPG, cholesterol and triolein at concentrations of 35.6 mg/mL, 6.225 mg/mL, 23.1 mg/mL, 6.5 mg/mL, respectively. PLA was from Sigma Chemical Company (St. Louis, Mo.), with a molecular weight of 106,000. A separate solution of leuprolide contained 6.0 mg/mL in water. DEPC, DPPG, and triolein were from Avanti Polar Lipids (Alabaster, Ala.) and cholesterol was from Spectrum Chemical Manufacturing Corp. (Gardena, Calif.). The leuprolide was from Bachem (Torrance, Calif.). The ratio of the volume of aqueous phase to the volume of volatile organic solvent phase was 5 mL to 5 mL. The "water-in-oil" emulsion was prepared by mixing on a Homo Mixer (Tokushu Kika Kogy Co., Ltd., Osaka, Japan) at a speed of 9000 rpm for 8 min. The second aqueous phase was a mixture of 5 wt. % glucose and 40 mM lysine. Spherules were formed by mixing at 4000 rpm for 1 min. A stream of nitrogen gas set at 50 psi for 20 minutes at 37° C. was flushed through the suspension of spherules to evaporate the chloroform. The suspending medium was exchanged with 0.9 wt % sodium chloride by washing and centrifuging at 600×g twice.

The mean particle diameter was determined on a laser scattering particle size distribution analyzer (Model LA-910, Horiba Instruments, Irvine, Calif.). The mean particle diameter for the lipid/polymer pharmaceutical composition was 15.9 µm.

The concentration of leuprolide in the pharmaceutical composition, and the supernatant of the pharmaceutical composition were determined by high pressure liquid chromatography (HPLC) (Model 1100, Hewlett-Packard, Irvine, Calif.) using a C-18 reverse phase primesphere column 4.6×250 mm (Phenomenex, Torrance, Calif.). The mobile phase consisted of a gradient of 75% solution A to 25% solution B at time 0, which increased to 100% solution B at 12 min. Solution A was 0.1% trifluoroacetic acid, and solution B was 0.1% trifluoroacetic acid. The peaks were monitored at 280 and 550 mm.

The 1.9:1 lipid/polymer pharmaceutical composition, unencapsulated leuprolide solution and 0.9% NaCl solution were administered by a subcutaneous injection in the lateral lower back to 400 g male Harlan Sprague Dawley albino rats. The number of animals per group was six. The dose was 3.6 mg per rat and the volume was 600 µL. Serum was collected via venipuncture (saphenous vein) from unanesthetized animals at 0, 1.5 hour, 1, 3, 7, 14, 28, 60, 88, 92, 106 days. The time points collected for the unencapsulated leuprolide group were 0, 1.5 hour, 1, 3, 7, 14 days. The serum samples were kept at −40° C. until analysis.

Serum testosterone levels were determined with a solid-phase radioimmunoassay (RIA) kit. The Coat-A-Count total testosterone kit was purchased from Diagnostic Products Corporation (Los Angeles, Calif.). The assay is designed for the quantitative measurement of testosterone in serum. The assay is based on testosterone specific antibody immobilized to the wall of a polypropylene tube. $^{125}$I-labeled testosterone competes for a fixed time with testosterone in the serum sample for antibody sites. The tube is then decanted, to separate the bound antibody from the free. The animal serum samples were counted in a gamma counter (Model 1175 Searle, Des Plaines, Ill.). The concentrations of serum testosterone were determined from a calibration curve, (log testosterone vs. log percent bound).

Figure 11:
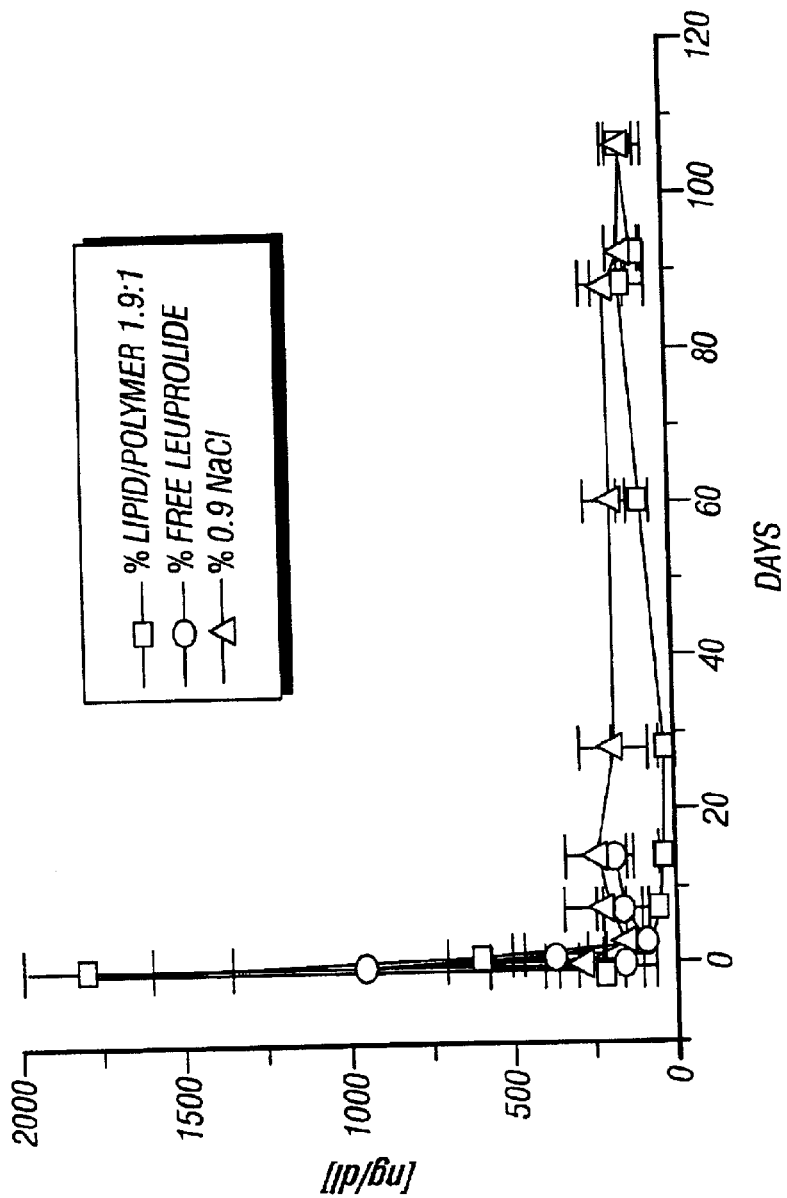
FIG. 11 is a plot of serum testosterone concentrations of varying times after subcutaneous administration of A) a solution of leuprolide in 1.9:1 lipid/polymer preparation, B) free leuprolide and C) 0.9% saline solution.

The serum testosterone concentrations (µg/dL) at different time points after subcutaneous administration for the three treatment groups are shown in FIG. 11. Data from day 3 to day 106 are plotted on an expanded scale in FIG. 12.

Figure 12:
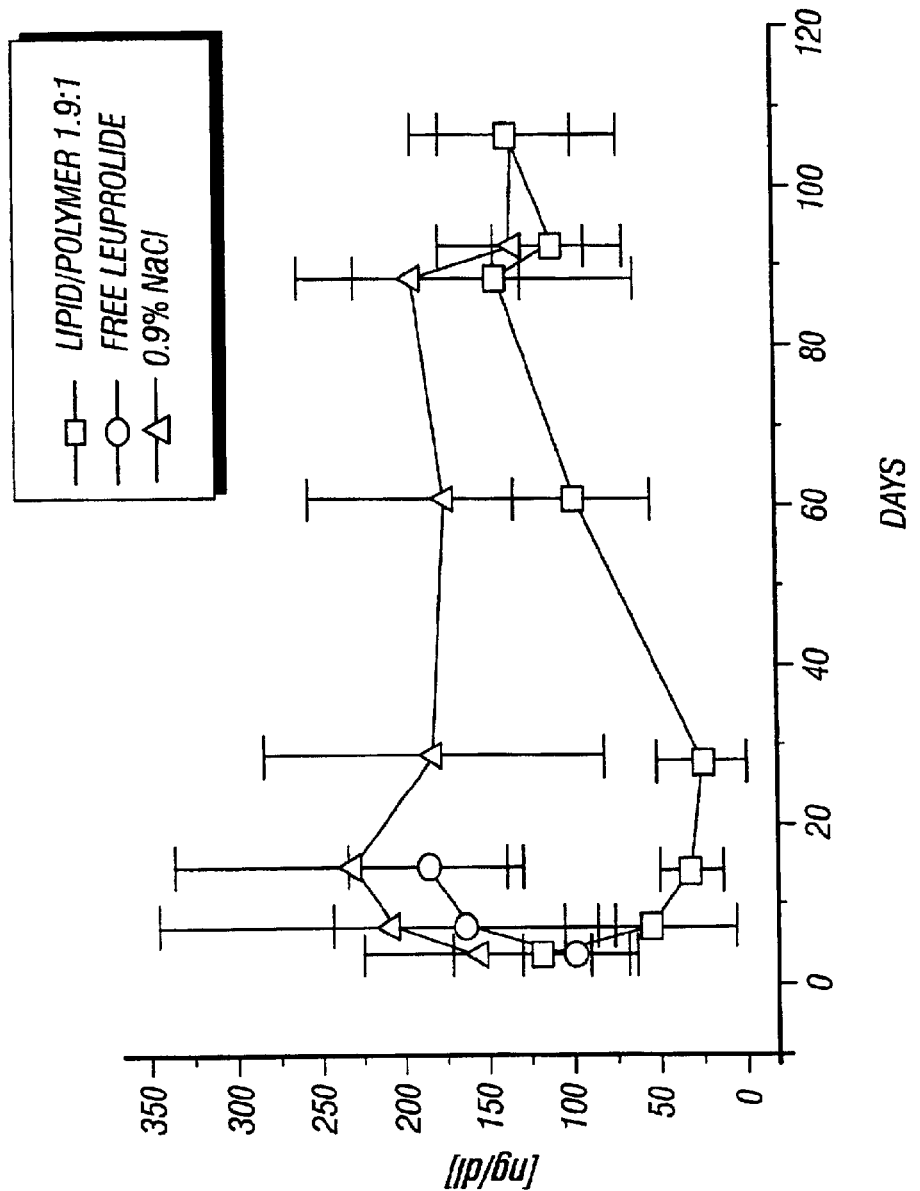
FIG. 12 is an expanded plot of FIG. 11.

FIGS. 11 and 12 (an expanded vertical scale) show sustained release of leuprolide for up to 80–90 days after parenteral administration of leuprolide-containing lipid/polymer microspheres.

Example 12

Preparation of the Pharmaceutical Composition

A lipid/polymer-containing pharmaceutical composition with lipid:polymer ratio 1:1.12 was prepared as in Example 1 with the following modifications. The aqueous solution contained 80 mg/mL amikacin, pH 8. For preparing the lipid/polymer-containing pharmaceutical composition with lipid to polymer ratio of 1:1.12 by weight, the chloroform solution is as described in Example 2. The chloroform solution contained the polymer poly (lactide-co-caprolactone) (PLC) at a concentration of 50 mg/mL, DOPC, DPPG, cholesterol and triolein at concentrations of 10.4 mg/mL, 2.1 mg/mL, 7.7 mg/mL, 2.2 mg/mL, respectively. PLC was from Birmingham Polymers Inc. (Birmingham, Ala.), with a lactide: caprolactone ratio of 75:25. DOPC, DPPG, and triolein were from Avanti Polar Lipids (Alabaster, Ala.) and cholesterol was from Spectrum Chemical Manufacturing Corp. (Gardena, Calif.). The ratio of the volume of aqueous phase to the volume of volatile organic solvent phase was 5 mL to 5 mL. The water-in-oil emulsion was prepared by mixing on a Homo Mixer (Tokushu Kika Kogyo Co., Ltd., Osaka, Japan) at a speed of 9000 rpm for 10 min. The second aqueous phase was a mixture of 5 wt. % glucose and 40 mM lysine. Spherules were formed by mixing at 6000 rpm for 1 min. A stream of nitrogen gas set at 50 psi for 20 minutes at 37 C was flushed through the suspension of spherules to evaporate the chloroform. The suspending medium was exchanged with 0.9 wt. %. sodium chloride by washing and centrifuging at 600×g twice.

The particle diameter was measured using a laser scattering particle size distribution analyzer (Model LA-910, Horiba Instruments, Irvine, Calif.) using the length weighed distribution base and a relative refractive index of 1.18–1.00 i. The mean particle diameter for the lipid/polymer pharmaceutical composition was 8.23 µm. The volume weighted mean particle size was 123.4 µm.

Example 13

Sustained Release in vivo of Encapsulated Physiologically Active Substance from Pharmaceutical Compositions after Interperitoneal Administration The pharmaceutical compositions were prepared by employing a double emulsification process. The "water-inoil" type emulsion was prepared from 5 mL of 25 mM arginine-glycine-glycine (Sigma, St. Louis, Mo.) buffer pH 7.9 containing 4 percent dextrose (Fisher, Fair Lawn, N.J.), and erythropoietin with 2.5 mg/mL human serum albumin (gift from UC San Diego Medical Center, San Diego, Calif.). The volatile organic phase contained lipids and polymer at a ratio of 1:1, with or without erythropoietin, or lipid/polymer ratio of 4:1 with erythropoietin. The water-immiscible solvent phase contained a mixture of phospholipids, cholesterol, triglycerides and PLGA (poly DL-lactide-co-glycolide). For the 1:1 (mass of lipid:mass of polymer) formulation, the solvent phase contained 10.4 mg/mL DOPC (dioleoyl phosphatidylcholine), 2.1 mg/mL DPPG (dipalnitoyl phosphatidylglycerol, sodium salt), 2.2 mg/mL triolein, all from Avanti Polar Lipids (Alabaster, Ala.), 7.7 mg/mL cholesterol (Spectrum, Garden, Calif.), and 22.4 mg/mL PLGA (Sigma, St. Louis, Mo.) dissolved in chloroform (Spectrum, Gardena, Calif.). For the 4:1 formulation the weight ratio of lipid to polymer was varied, keeping the total concentration of lipid plus polymer constant. The mixing speed and time for producing the "water-in-oil" type emulsion was 9,000 rpm for 8 minutes on a Homo Mixer (Tokoshu Kika Kogyo Co., Ltd., Osaka, Japan). The second aqueous phase was 20 mL of a solution containing 4% glucose (McGaw, Irvine, Calif.) and 40 mM lysine (Degussa, Courbevoie, France). The second aqueous phase was added to the "water-in-oil" suspension and mixed at 4,000 rpm for 1 minute. The organic solvent was removed by slow shaking at 37° C. with nitrogen gas passing at 50 liters/minute for 20 minutes. The suspending medium was exchanged with 25 mM argenine-glycine-glycine buffer pH 7.9 by washing and centrifuging at 600×g twice.

The mean particle diameters were determined on a laser scattering particle size distribution analyzer (Model LA-910, Horiba Instruments, Irvine, Calif.). The mean particle diameters were 26.1 µm, 23.1 µm, 24.5 µm for the 1:1 and 4:1 lipid/polymer pharmaceutical compositions, and the 1:1 lipid/polymer blank respectively.

The concentration of erythropoietin in the pharmaceutical composition was determined by quantitative colorimetric sandwich ELISA (R&D Systems, Minneapolis, Minn.) for human erythropoietin. Plates were read on an EL312E microplate, Bio-Kinetics reader (Bio-Tek Instruments, Winooski, Vt.) at 450 nm wavelength for detection. The concentration of human serum albumin (HSA) in the blank was determined by high pressure liquid chromatography (HPLC) (Model 1100, Hewlett-Packard, Irvine, Calif.) using a C18 protein and peptide column 4.6 X 250 mm (Vydac, Hespena, Calif.). The mobile phase consisted of a gradient of 5% solution A to 80% solution B in 18 minutes. Solution A was 0.1% triflouroacetic acid (TFA)(Pierce, Rockford, Ill.) in HPLC water from Mallinckrodt (Paris, Ky.), and solution B was 0.1% TFA in methanol from Burdick & Jackson (Muskegon, Mich.) with a flow rate of 1 mL per minute. The peaks were monitored at 280 nm wavelength.

Concentration of the pharmaceutical composition and unencapsulated erythropoietin were adjusted to 500 IU of erythropoietin with arginine-glycine-glycine buffer at pH 7.9. Blank was adjusted to contain 0.4 mg/mL of HSA protein. Five female CD1/ICR Harlan Sprague Dawley mice weighing 28–32 grams were injected intraperitoneal (IP) for each pharmaceutical composition. The dose was 500 IU erythropoietin in a 1 mL total volume. Blood was collected via the orbital sinus from animals anesthetized with 2.5% Halothane and IL/minute oxygen. Hematocrits were taken on days 0, 1, 3, 6, 10, 13, 17, 21, 24. Blood was collected directly into capillary tube and spun for 6 minutes on a hematocrit centrifuge.

Figure 13:
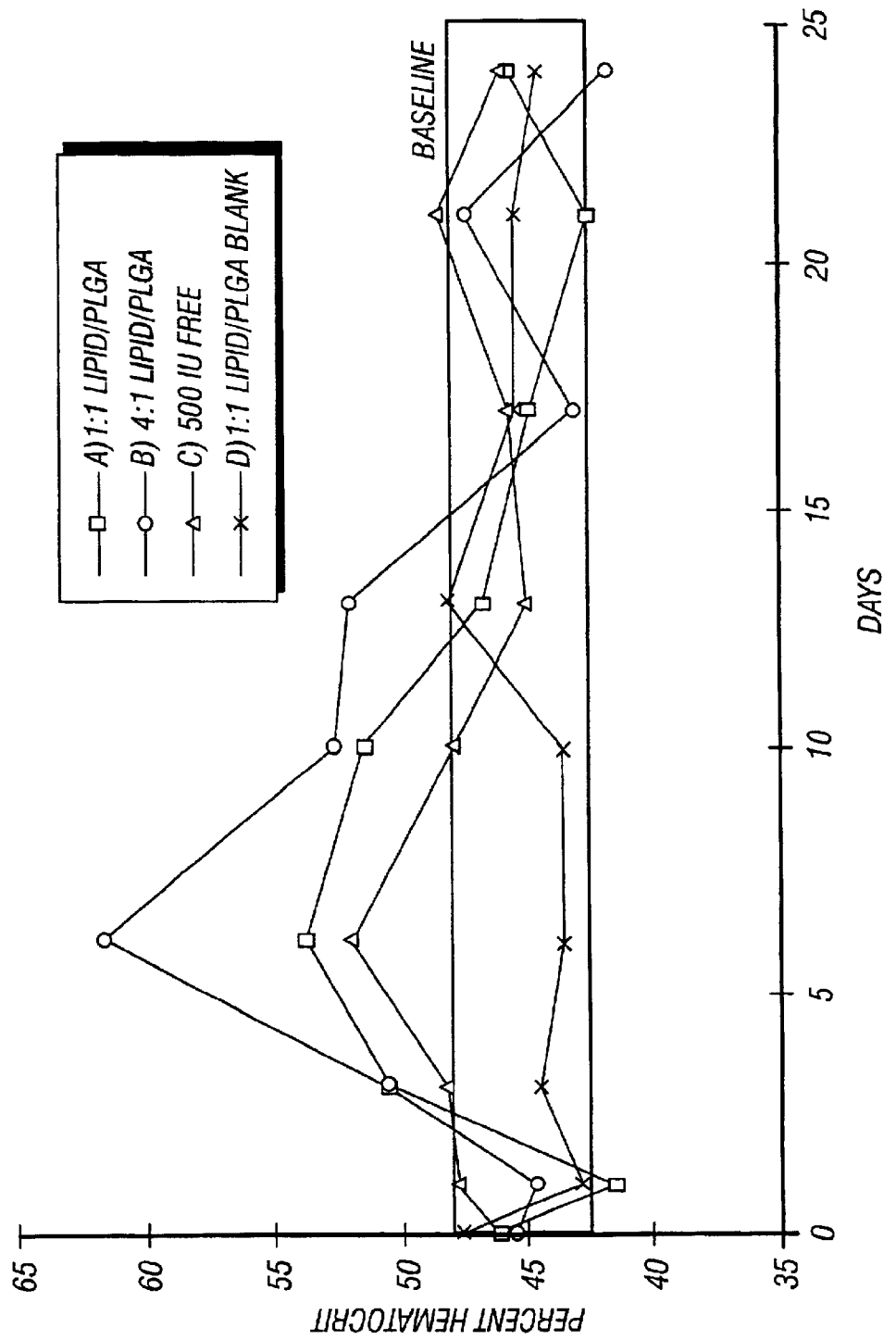
FIG. 13 is a plot of increase in hematocrit at various times after intraperitoneal administration of 500 IU of erythropoietin as A) 1:1 lipid/polymer preparation B) 4:1 lipid/polymer preparation C) free erythropoietin, and D) 1:1 lipid/polymer blank.

The results in FIG. 13 show sustained effect of hematocrit for up to 13 days with the 4:1 lipid/polymer pharmaceutical composition and up to 10 days for the 1:1 lipid/polymer pharmaceutical composition.

The increase in hematocrit resulting from an injection of free (unencapsulated) erythropoietin is not as pronounced as with the encapsulated drug. Injected free (unencapsulated) erythropoietin resulted in this effect lasting only up to 6 days. The 4:1 lipid:polymer composition shows a 15.6 percent increase in hematocrit in comparison to unencapsulated drug. The 1:1 pharmaceutical composition shows a 7.8 percent in hematocrit in comparison to unencapsulated drug. The 4:1 lipid:polymer pharmaceutical composition resulted in the highest hematocrit overall.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for producing biodegradable lipid/polymer-containing compositions, the process comprising:
   a) forming a "water-in-oil" emulsion from a first aqueous phase and a volatile organic solvent phase comprising at least, one volatile organic solvent, at least one biodegradable polymer or copolymer which is soluble in organic solvent, and at least one lipid;
   b) dispersing the "water-in-oil" emulsion into a surfactant-free second aqueous phase to form solvent spherules, and
   c) removing the volatile organic solvent from the solvent spherules to form a microsphere composition suspended in the second aqueous phase, wherein the boundary of the microsphere compartment comprises the biodegradable lipid/polymer.

2. A process for producing biodegradable lipid/polymer-containing pharmaceutical compositions, the process comprising:
   a) forming a "water-in-oil" emulsion from a first aqueous phase comprising at least one hydrophilic physiologically active substance, and a volatile organic solvent phase comprising at least one volatile organic solvent, at least one biodegradable polymer or copolymer which is soluble in organic solvent, and at least one lipid;
   b) dispersing the "water-in-oil" emulsion into a surfactant-free second aqueous phase to form solvent spherules; and
   c) removing the volatile organic solvent from the solvent spherules to form a pharmaceutical microsphere composition suspended in the second aqueous phase, wherein the boundary of the microsphere compartment comprises the biodegradable lipid/polymer, and wherein the lipid:polymer ratio is chosen to modulate the in vivo release rate of the physiologically active substance.

3. The process of claim 2, further comprising removing substantially all of the organic solvent from the solvent spherules.

4. A pharmaceutical composition produced by the process of claim 2.

5. A process for producing biodegradable lipid/polymer-containing pharmaceutical compositions, the process comprising:
   a) forming a "water-in-oil" emulsion from a first aqueous phase, and a volatile organic solvent phase comprising at least one hydrophobic physiologically active substance, at least one volatile organic solvent, at least one biodegradable polymer or copolymer which is soluble in organic solvent, and at least one lipid;

b) dispersing the "water-in-oil" emulsion into a surfactant-free second aqueous phase to form solvent spherules; and c) removing the volatile organic solvent from the solvent spherules to form a pharmaceutical microsphere composition suspended in the second aqueous phase, wherein the boundary of the microsphere compartment comprises the biodegradable lipid/polymer, and wherein the lipid:polymer ratio is chosen to modulate the in vivo release rate of the physiologically active substance.

6. The process of claim 5, further comprising removing substantially all of the organic solvent from the solvent spherules.

7. A lipid/polymer-containing pharmaceutical composition produced according to the process of claim 5.

8. The process of claim 2, wherein the volatile organic solvent phase further comprises at least one tryglyceride.

9. A composition produced according to the process of claim 1.

* * * * *

UNITED STATES PATENT AND TRADEMARK OFFICE
CERTIFICATE OF CORRECTION

PATENT NO. : 6,793,938 B2
DATED : September 21, 2004
INVENTOR(S) : Mantripragada Sankaram It is certified that error appears in the above-identified patent and that said Letters Patent is hereby corrected as shown below:

Title Page,
Item [56], References Cited, U.S. PATENT DOCUMENTS, change "5,808,573 A 9/1998 Shih et al." to -- 5,807,573 A 9/1998 Ljusberg-Wahren et al. --

Column 4, Line 67 to Column 5, Line 1,
Change "in viva" to -- in vivo --

Signed and Sealed this

Third Day of May, 2005

JON W. DUDAS
*Director of the United States Patent and Trademark Office*